United States Patent
Izzetoglu et al.

(10) Patent No.: US 10,499,838 B2
(45) Date of Patent: Dec. 10, 2019

(54) NON-INVASIVE BRAIN WATER MONITORING DEVICE FOR CEREBRAL EDEMA AND CEREBRAL AUTOREGULATION MONITORING SYSTEM AND METHOD

(71) Applicant: Drexel University, Philadelphia, PA (US)

(72) Inventors: Meltem Izzetoglu, Bryn Mawr, PA (US); Juan Du, Broomall, PA (US); Baruch Ben Dor, Radnor, PA (US)

(73) Assignee: Drexel University, Philadelphia, PA (US)

( * ) Notice: Subject to any disclaimer, the term of this patent is extended or adjusted under 35 U.S.C. 154(b) by 366 days.

(21) Appl. No.: 15/136,899

(22) Filed: Apr. 23, 2016

(65) Prior Publication Data
US 2016/0310054 A1    Oct. 27, 2016

Related U.S. Application Data

(60) Provisional application No. 62/152,377, filed on Apr. 24, 2015.

(51) Int. Cl.
*A61B 5/1455* (2006.01)
*A61B 5/01* (2006.01)
*A61B 5/00* (2006.01)

(52) U.S. Cl.
CPC ........ *A61B 5/14553* (2013.01); *A61B 5/0075* (2013.01); *A61B 5/01* (2013.01); *A61B 5/4064* (2013.01); *A61B 5/4878* (2013.01); *A61B 5/6814* (2013.01); *A61B 5/6833* (2013.01); *A61B 5/14552* (2013.01); *A61B 2562/166* (2013.01)

(58) Field of Classification Search
None
See application file for complete search history.

(56) References Cited

U.S. PATENT DOCUMENTS

| | | |
|---|---|---|
| 5,779,631 A | 7/1998 | Chance |
| 5,954,053 A | 9/1999 | Chance et al. |
| 6,526,309 B1 | 2/2003 | Chance |
| 7,643,858 B2 | 1/2010 | Agashe et al. |
| 8,060,189 B2 | 11/2011 | Ben Dor et al. |
| 8,135,448 B2 | 3/2012 | Baker, Jr. et al. |
| 8,280,484 B2 | 10/2012 | Boyden et al. |
| 8,320,996 B2 | 11/2012 | Panasyuk et al. |
| 8,509,866 B2 | 8/2013 | Schmitt et al. |

(Continued)

OTHER PUBLICATIONS

Colier et al. (Simultaneous near-infrared spectroscopy monitoring of left and right occipital areas reveals contra-lateral hemodynamic changes upon hemi-field paradigm; 1999).*

(Continued)

*Primary Examiner* — David J. McCrosky
*Assistant Examiner* — Jay B Shah
(74) *Attorney, Agent, or Firm* — Howson & Howson LLP

(57) ABSTRACT

A system, device and methods for quantitatively monitoring and evaluating changes in water and hemoglobin content in the brain in a non-invasive manner are provided. The system may be used for real-time detection and monitoring of brain edema and/or for an assessment of cerebral autoregulation.

2 Claims, 26 Drawing Sheets

(56) References Cited

U.S. PATENT DOCUMENTS

| | | | |
|---|---|---|---|
| 8,954,133 B1 | 2/2015 | Hanlon et al. | |
| 2002/0016536 A1* | 2/2002 | Benni | A61B 5/14552 600/323 |
| 2002/0049389 A1* | 4/2002 | Abreu | A61B 3/1241 600/558 |
| 2005/0165316 A1* | 7/2005 | Lowery | A61B 5/14532 600/480 |
| 2011/0118572 A1* | 5/2011 | Bechtel | A61B 5/0059 600/322 |
| 2014/0081093 A1* | 3/2014 | Kim | A61B 5/0075 600/301 |
| 2014/0296693 A1 | 10/2014 | Binder et al. | |
| 2014/0343384 A1 | 11/2014 | Floyd et al. | |

OTHER PUBLICATIONS

Almajidy et al. (On the design of a multi-channel NIR system to monitor functional brain activity; 2013).*

Bunce et al. (Functional Near-Infrared Spectroscopy; 2006).*

Strojnik et al. Spectral dependence of absorption sensitivity on concentration of oxygenated hemoglobin: pulse oximetry implications; Journal of Biomedical Optics 18(10), 108001 (Oct. 2013) (Year: 2013).*

J.R. Thiagarajah et al., "Noninvasive early detection of brain edema in mice by near-infrared light scattering", Journal of Neuroscience Research, vol. 80, No. 2, pp. 293-299, 2005 (month unknown).

M. Izzetoglu et al., "Functional near-infrared Neuroimaging", IEEE Trans. on Neural Systems and Rehabilitation Engineering, vol. 13, No. 2, pp. 153-159, Jun. 2005.

M. Izzetoglu et al, "Motion artifcat cancellation in NIR spectroscopy using discrete Kalman filtering", BioMedical Engineering OnLine, 9:16, Mar. 2010.

V.S. Langford et al., "Temperature dependence of the visible near-infrared absorption spectrum of liquid water", The Journal of Physical Chemistry A, 105(39), pp. 8916-8921, Sep. 2001.

A. Marmarou, "A review of progress in understanding the pathophysiology and treatment of brain edema", Neurosurg Focus, 22(5):E1, May 2007.

J. Mocco et al., "Potential mechanisms and clinical significance of global cerebral edema following aneurysmal subarachnoid hemorrhage", Neurosurg Focus 22(5):E7, May 2007.

A. Raslan et al., "Medical Management of Cerebral Edema", Neurosurg Focus, 22(5):E12, May 2007.

R. Sfareni et al., "Near Infrared absorption spectra of humandeoxy- and oxyhaemoglobin in the temperature range 20-40 C", Biochimica et Biophysics Acta (BBA), Protein Structure and Molecular Enzymology, 1340(2), pp. 165-169, Jul. 1997.

R. Thiex et al., "Brain edema after intracerebral hemorrhage: mechanisms, treatment options, management strategies and operative indications", Neurosurg Focus, 22(5):E6, May 2007.

K. Uludag et al., "Cross talk in the Lambert-Beer calculation for near infrared wavelengths estimated by Monte Carlo simulations", Journal of Biomedical Optics, 7(1), pp. 51-59, Jan. 2002.

A.W. Unterberg et al., "Edema and Brain Trauma", Neuroscience, vol. 129, pp. 1021-1029, 2004 (month unknown).

H. Zhao et al., "Maps of optical differential pathlength factor of human adult forehead, somatosensory motor and occipital regions at multi-wavelenghts in NIR", Physics in Medicine and Biology, vol. 47, pp. 2075-2093, Jun. 2002.

K. Zweckberger et al., "Effect of Decompression Craniotomy on increase of Contusion Colume and Functional Outcome after Controlled Cortical Impact in mice", Journal of Neurotrauma, vol. 20, No. 12, pp. 1307-1314, Dec. 2003.

* cited by examiner

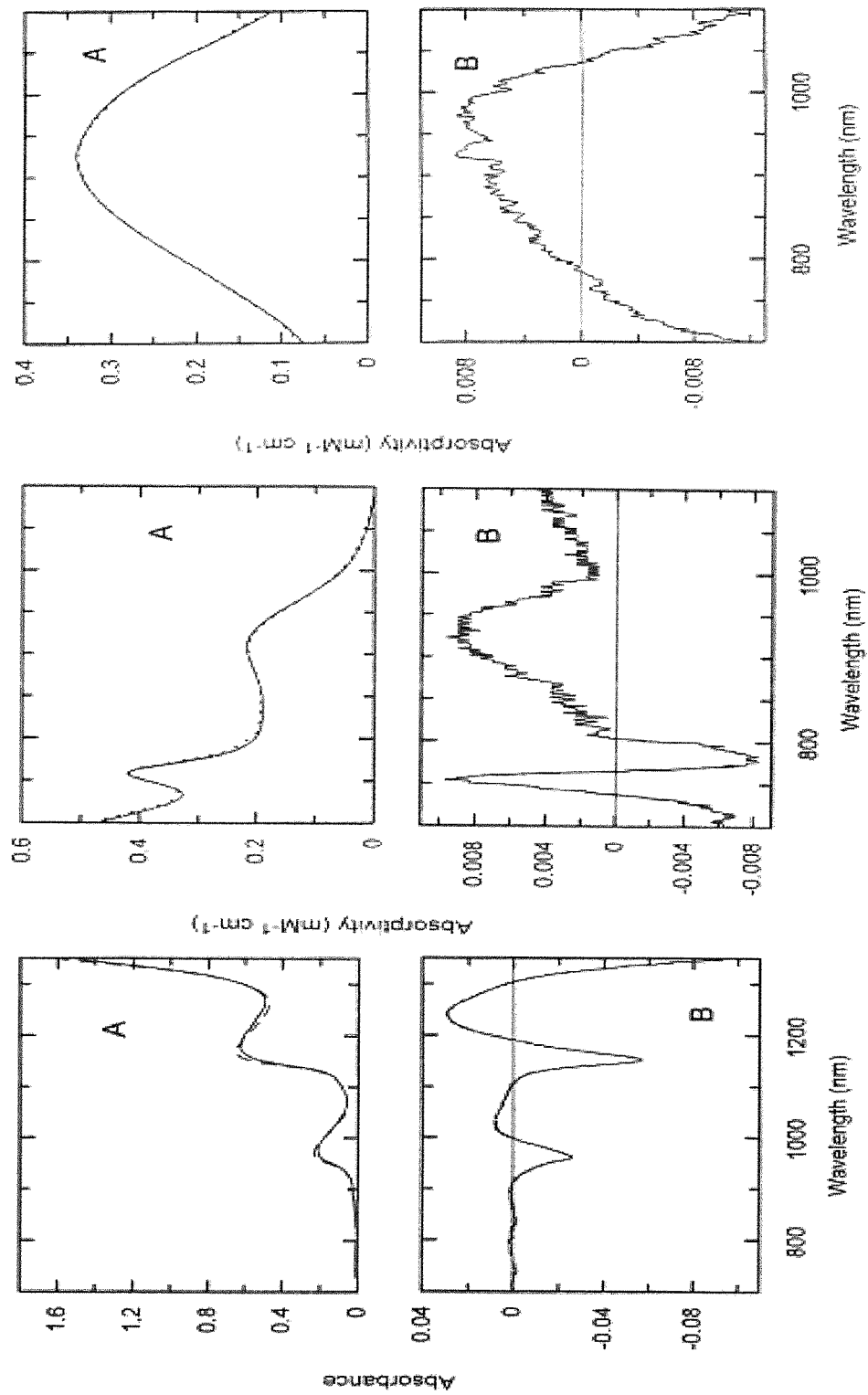

FIG. 11
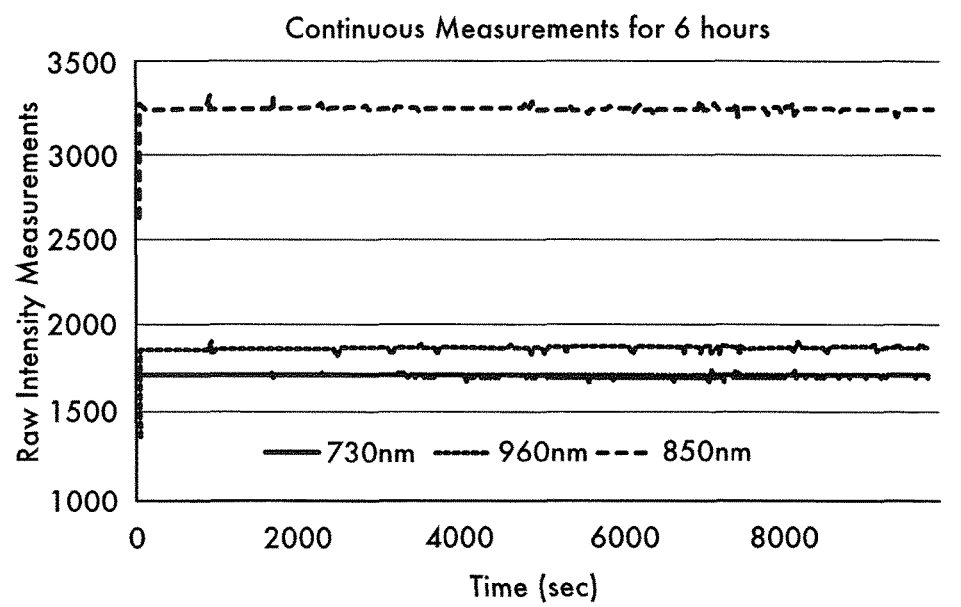
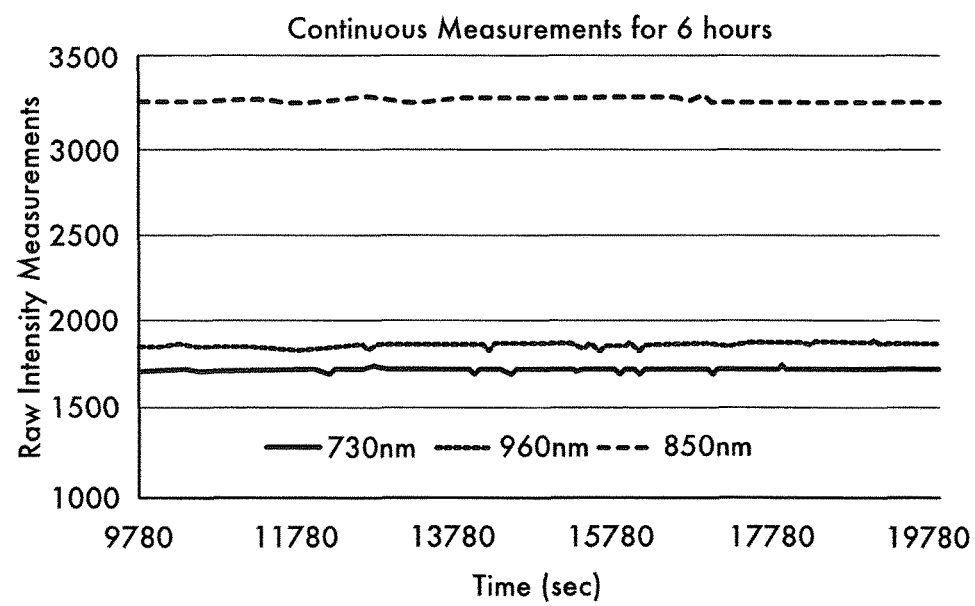

FIG. 12
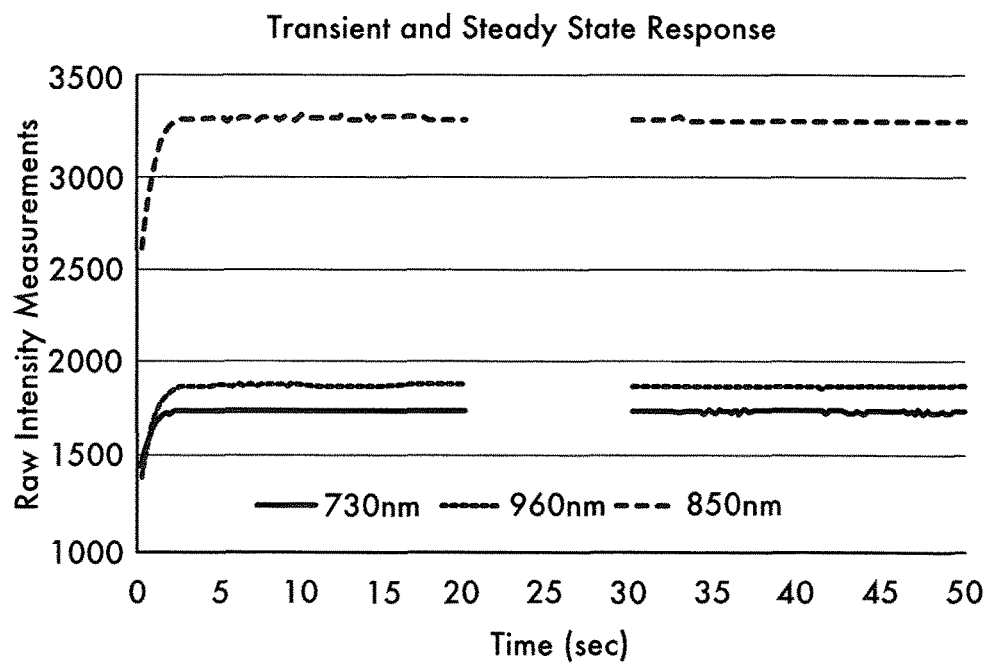
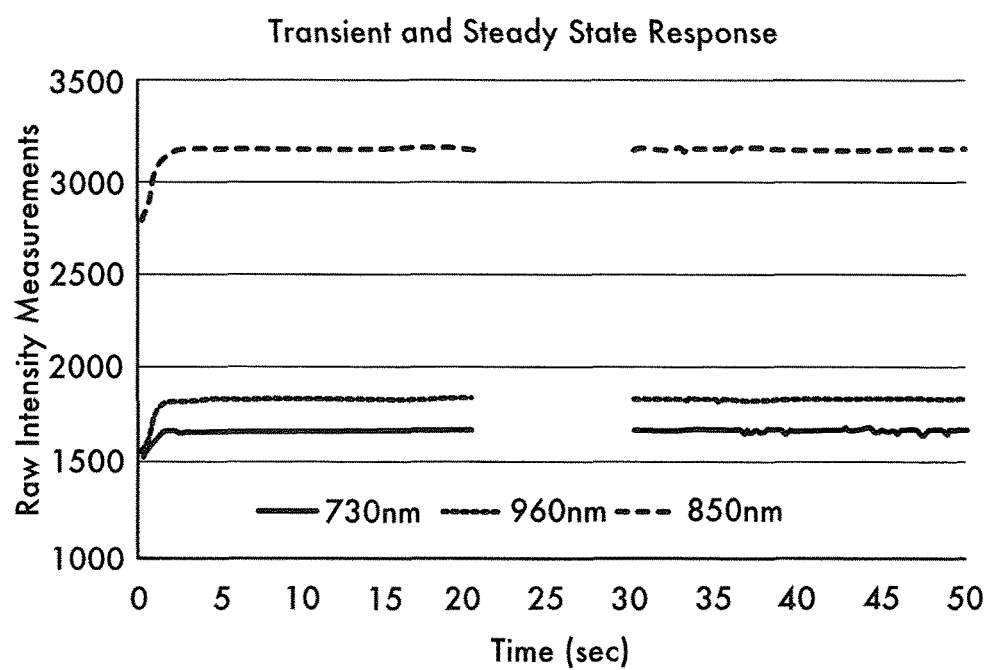

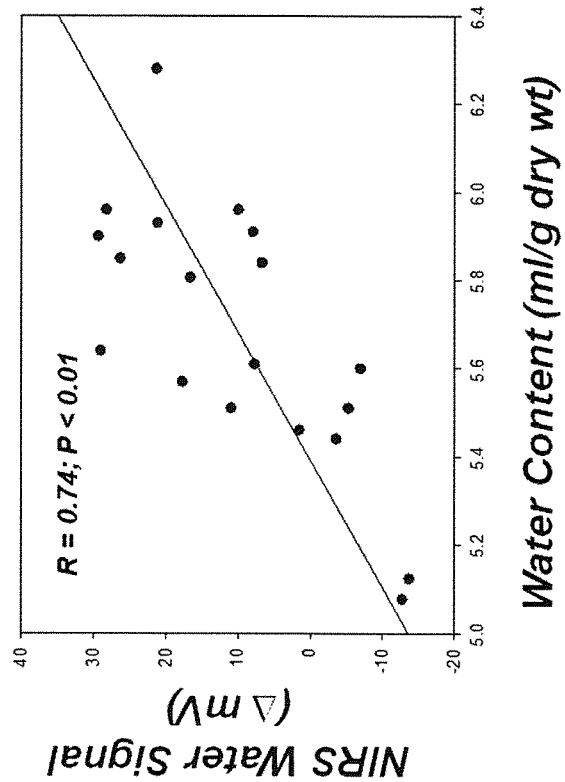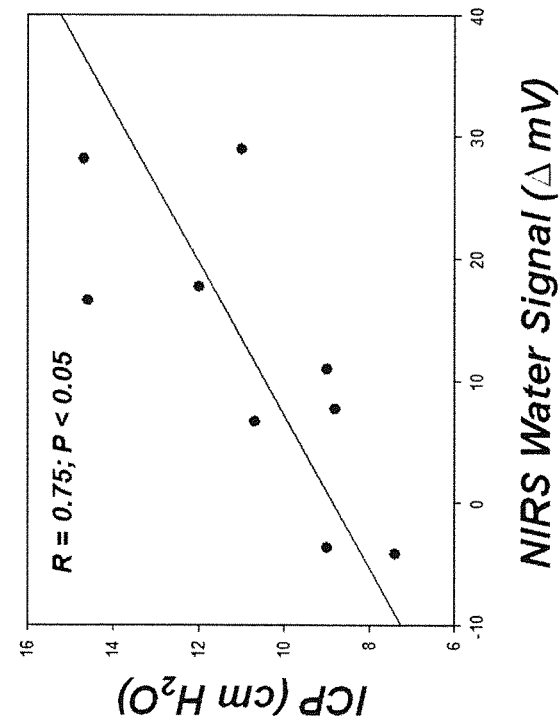
FIG. 41

NON-INVASIVE BRAIN WATER MONITORING DEVICE FOR CEREBRAL EDEMA AND CEREBRAL AUTOREGULATION MONITORING SYSTEM AND METHOD

CROSS REFERENCE TO RELATED APPLICATIONS

This application claims the benefit under 35 USC § 119(e) of U.S. Provisional Patent Application No. 62/152,377, filed Apr. 24, 2015.

STATEMENT REGARDING FEDERALLY SPONSORED RESEARCH OR DEVELOPMENT

This invention was made with government support under Contract No. W81XWH-08-2-0573 awarded by the U.S. Army, Telemedicine and Advanced Technology Research Center (TATRC). The government has certain rights in this invention.

BACKGROUND

Brain edema is the accumulation of fluid in the brain and resultant swelling of the brain. Causes of brain edema may include trauma, a tumor, exposure to toxic substances, and other injuries. About 1.7 million people in an average year in the U.S. incur a head injury requiring medical care and about 38,000 die from head injury before being admitted to a hospital.

Brain damage may also be the result of a lack of oxygen. For instance, hypoxic-ischemic encephalopathy, or HIE, is a condition that occurs when the brain has been deprived of an adequate oxygen supply. Infants that have incured hypoxic-ischemic encephallopathy (HIE) constitute about 23% of neonatal deaths worldwide.

Current clinical practice for the treatment of brain edema cases is to use an invasive procedure called craniotomy. Experimental evidence for the beneficial or detrimental role of decompression craniotomy after traumatic brain injury are scarce. Recent researches and studies on mice suggest that a craniotomy may be a useful therapeutic option after traumatic brain injury (TBI) in humans, provided that it is applied early.

In infants with hypoxic-ishemic encephalopathy, therapeutic hypothermia is more beneficial for edema reduction if applied early. In spite of improvements in outcome since the introduction of therapeutic hypothermia as a treatment modality, 55% of treated infants die or have adverse neurodevelopmental outcomes. Additional neuroprotective strategies are needed for improving the outcomes of affected infants.

The detection of edema may be based on computed tomography (CT) scans or magnetic resonance imaging (MRI). However, since both CT and MRI are expensive, not every medical facility has such equipment. Also, since such equipment is not portable and CT has radiation exposure, such equipment cannot be used in the field or for continuous, bedside monitoring. Once edema is detected, its progression is usually monitored by using an intracranial pressure (ICP) monitoring sensor which is invasive and can cause complications.

Early detection of brain edema can help clinicians in the timely identification of patients that are in need of surgery or other types of therapy and thus, improve the outcome of such therapies. Thus, early detection of brain edema may be effective for reducing the development of more serious brain injury and related disabilities and can lessen the costs of treating a brain injury.

In addition, the ability to monitor cerebral autoregulation may provide important information for the care of some patients. Cerebral autoregulation is the physiological mechanism that maintains cerebral blood flow at an appropriate level during changes in blood pressure. By way of example, an accurate assessment of cerebral autoregulation may guide in the selection and level of treatment regimes from mild to intense using hypothermia to drug treatments and hence improve treatment outcomes and quality of life of patients.

BRIEF DESCRIPTION OF THE DRAWINGS

Various features of the embodiments described in the following detailed description can be more fully appreciated when considered with reference to the accompanying figures, wherein the same numbers refer to the same elements.

FIG. 4 is a graph showing temperature dependence of phosphate buffered saline, wherein "A" represents absolute spectra at 20° C. (via continuous line) and at 40° C. (via dashed line) and in which "B" represents a difference spectrum (40-20° C.).

FIG. 5 is a graph showing temperature dependence of Hb, wherein "A" represents absolute spectra at 20° C. (via continuous line) and at 40° C. (via dashed line) and in which "B" represents a difference spectrum (40-20° C.).

FIG. 6 is a graph showing temperature dependence of $HbO_2$, wherein "A" represents absolute spectra at 20° C. (via continuous line) and at 40° C. (via dashed line) and in which "B" represents a difference spectrum (40-20° C.).

FIG. 11 is a graph showing continuous intensity measurements using the monitoring system of FIG. 10 for a 6 hour period.

FIG. 12 represents intensity measurements using the monitoring system of FIG. 10 during the first 50 seconds of a 6 hour drift test and the first 50 seconds of a 3 hour drift test.

FIG. 41 is graphs showing correlations between NIRS-derived water signal and ICP and wet/dry ratio measurements.

DETAILED DESCRIPTION

Figure 1:
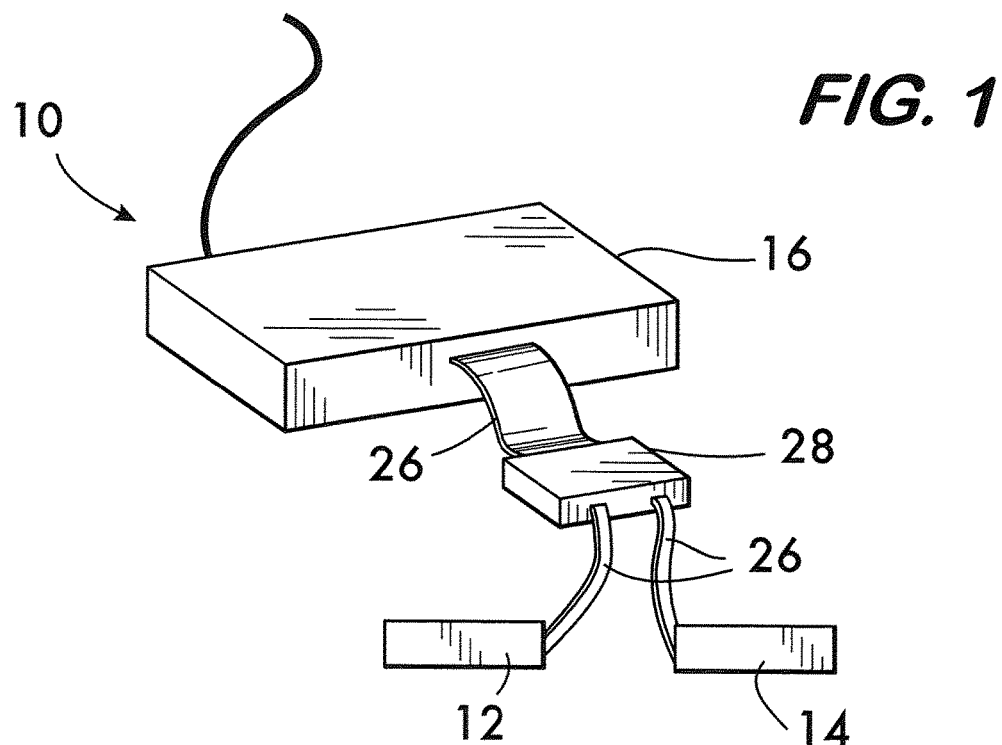
FIG. 1 is a perspective view of a part of a system for monitoring brain edema and/or for assessing cerebral autoregulation according to an embodiment.

For simplicity and illustrative purposes, principles of embodiments are described herein by referring primarily to examples thereof. In the following description, numerous specific details are set forth to provide a thorough understanding of the embodiments. It will be apparent to one of ordinary skill in the art that the embodiments may be practiced without limitation to these specific details. In some instances, well known methods and structures have not been described in detail so as not to unnecessarily obscure the embodiments.

"Patient" or "subject" as used herein means a mammalian animal, including a human, a veterinary or farm animal, a domestic animal or pet, and animals normally used for clinical research. More specifically, the subject of these methods, systems and devices is a human.

According to an embodiment, a system, device and method for quantitatively monitoring and evaluating changes in water and hemoglobin content in the brain in a non-invasive manner are provided. Such a system or device may be used for real-time detection and monitoring of brain edema and/or for an assessment of cerebral autoregulation.

Embodiments may be provided in the form of a relatively affordable, hand-held, non-invasive, portable, detection and monitoring device that is able to significantly enhance and aid current clinical practices and treatments of patients. For instance, the device may be able to help first responders and other clinicians to make rapid and accurate on-site clinical decisions for treatment of patients with brain edema or other brain damage. As one contimplated example, the device may be beneficial for military use where early detection and rapid treatment of brain edema, one of the most common blast related injuries in the battlefield, is critical to prevent development of severe brain injury.

In addition, embodiments of the device and method may provide important information relative to the experience of a prior hypoxic event by a patient which is not otherwise possible with any existing methodologies. Existence of a hypoxic event can guide therapeutic procedures including their selection and intensity. Without such knowledge, doctors and other care givers may only monitor immediate vital signs and attempt to make judgements on the administration of different form of therapies according to the vital signs and their related outcomes by trial and error. In contrast, with device and method of the embodiments disclosed herein, doctors and other care givers may monitor signal changes as measured by the non-invasive device which will be representative of cerebral autoregulation after the administration of different medications for some period of time, for instance, in a matter of minutes. In this manner, the doctor may be able to determine if a hypoxic event had taken place at a prior time and select a most appropriate type and amount of therapy and continue to monitor their outcomes by monitoring not just the vital signs, but also, changes in cerebral autoregulation.

According to one contemplated embodiment, the device may be a near-infrared (NIR) based device that relies on optical techniques derived from the physical principles of light absorption and reflectance to detect changes in the water and oxygenated (oxyHb) and deoxygenated hemoglobin (deoxyHb) content in the brain. Most biological tissues are relatively transparent to light in the NIR range between about 700-1000 nm, which is commonly referred to as an optical window. This is primarily due to the fact that within this optical window, the absorbance of the main constituents in human tissue (i.e. water, oxyHb and deoxyHb) is small, allowing light to penetrate the tissue. Fortunately, the absorption spectra of water, oxyHb and deoxyHb in the optical window remain significantly different from each other, which allows spectroscopic separation of these compounds to be possible via the use of a few sample wavelengths.

Thus, according to an embodiment, a device may operate at wavelengths tuned for the extraction of water and hemoglobin concentration within the brain. Since hemoglobin content can change, for example, due to hematoma development together with changes in the water content due to edema, the device may be designed to monitor the changes in all of these absorbers simultaneously. By way of example, the NIR-based monitoring sensor may house one or more light sources that irradiate light at wavelengths, for instance, of 730 nm (for deoxyHb concentration extraction), 850 nm (for oxyHb concentration extraction) and 940 or 960 nm (for water concentration extraction) and photodetectors to detect the light after it interracts with tissue.

The device may also house a temperature measurement mechanism, for instance, a built-in thermistor, to guide in selection of appropriate parameters in algorithms for correct extraction of the above referenced chromophore. Since fever may occur in patients with edema development and since hypothermia may be used as a treatment technique for HIE patients, changes in temperature may be taken into account for reliable measurement of changes in oxyHb, deoxyHb and water content of such patients.

The device may also have and apply appropriate algorithms for the identification and correction of signal changes in device measurements that may be due to the positioning of an unconscious, critically ill patient where the laying position of the patient (on their back or side) may be required to be adjusted frequently during their stay in an intensive care unit. This and other additional algorithms may be used to increase the reliability and effectiveness of measurements taken by the device.

System Components

The system may be in the form of a portable, point of care, near-infrared (NIR) based imaging device that utilizes various hardware components and applies various advanced algorithms that may be designed for different purposes, such as to rapidly detect and monitor brain edema and assess cerebral autoregulation. An example of a system 10 is best shown in FIG. 1-3.

The main components of the system 10 include one or more lightweight probes or sensors that may be designed to cover the forehead of a patient and/or parts thereof. As an example, a pair of separate and identical sensors, such as left probe 12 and right probe 14, is shown in FIG. 1. The system 10 may also include a control box 16 for data acquisition, a power supply for the control box (not shown), and a computer or electronic processing device 18 having or providing access to data analysis software. As shown in FIG. 3, the computer 18 may have a display for displaying and presenting measurements taken by the device.

Figure 2:
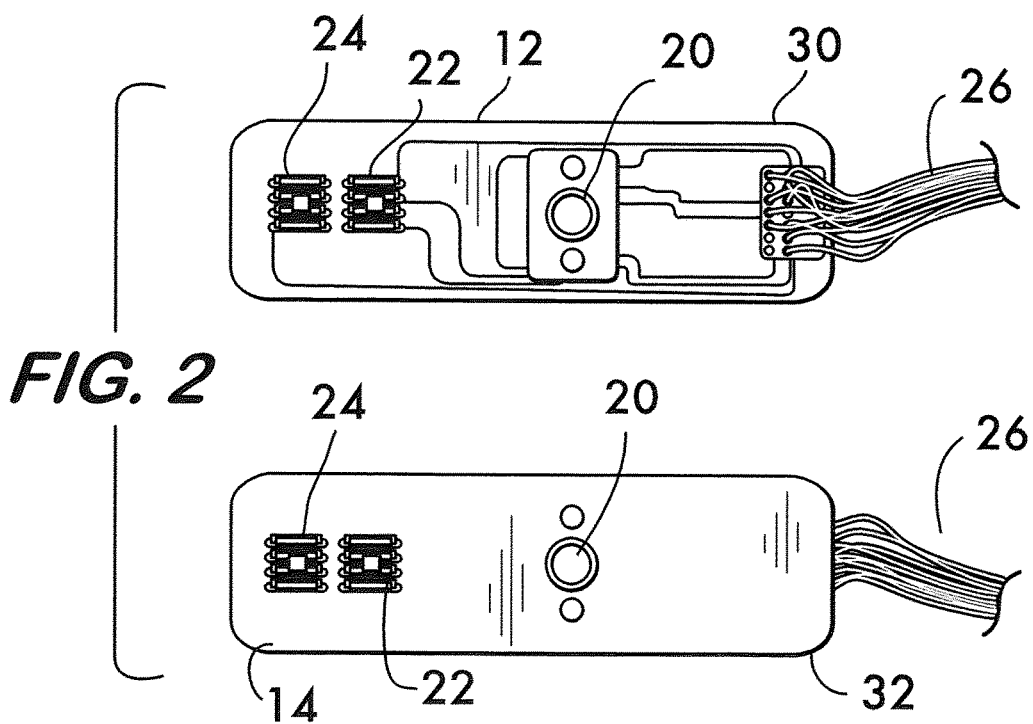
FIG. 2 is an elevational view of separate and identical left and right sensors or probes of the system of FIG. 1.
Figure 3:
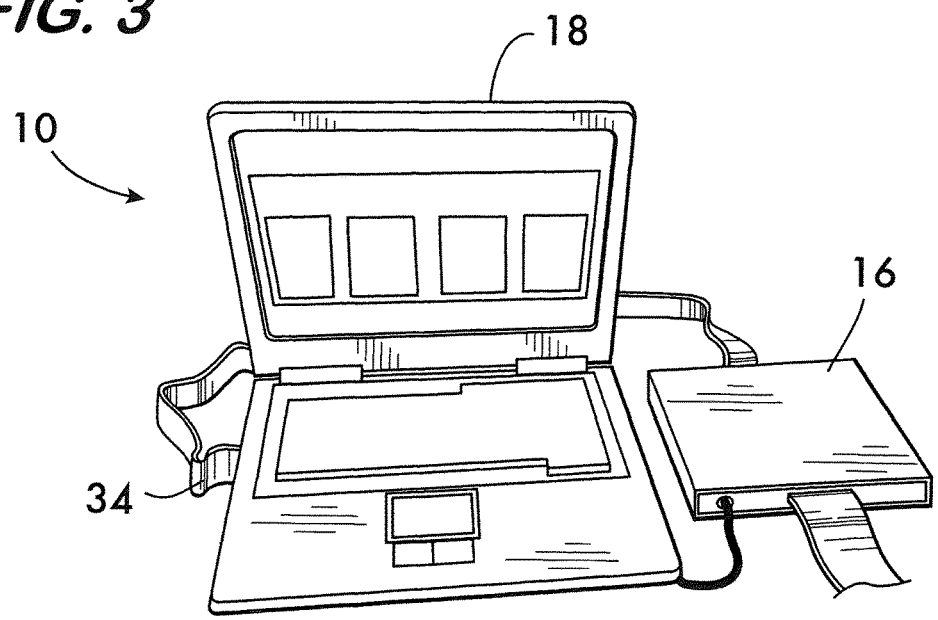
FIG. 3 is a perspective view of a control box, data acquisition card, and presentation computer of the system of FIG. 1.

As best shown in FIG. 2, each of the sensors, 12 and 14, has at least one LED light source 20 and two light detectors, 22 and 24, that may be spaced, for instance, 3 cm and 4 cm, respectively, from the light source 20. In use, one of the sensors 12 is adapted to be placed on a left side of the patient's forehead and the other sensor 14 is adapted to be placed on a right side of the forehead. As best shown in FIG. 1, each of the sensors, 12 and 14, may be connected to the control box 16 via wires 26 via an intermediate unit 28 housing signal splitters and/or thermal shutdown circuits. Of course, the sensors or any of the other components may also be adapted to communicate via wireless communications and various ones of the units may be combined and housed in a single unit or provided as separate units and/or be provided by one of more electronic processing units.

Each of the sensor, 12 and 14, may be flexible and provided in the form of a modular design consisting of two parts: an identical, reusable, flexible circuit board 30 (see FIG. 2) that carries infrared sources and detectors; and a disposable, single-use cushioning material 32 that serves to attach the sensor to the forehead of the patient, for instance, with a medical grade adhesive tape. In FIG. 2, the left probe 12 is shown with cushioning material removed and the right probe 14 is shown with cushioning material applied. The cushioning material may be a black foam material for providing comfortable usage and sealing for possible light and electrical leakage.

The flexible circuit of the sensors/probes provides a reliable integrated wiring solution, as well as enables consistent and reproducible component spacing and alignment. Because the circuit board and cushioning material are flexible, the components are able to move and adapt to various contours of the front of the patient's forehead, thus allowing the sensor elements to maintain an orthogonal orientation to the skin surface, which dramatically improves light coupling efficiency and signal strength. As an alternative, the pair of sensors, 12 and 14, may be provided in the form of a single full head version of a flexible sensor that may extend on both the right and left sides of the forehead as a single continuous unit. The area of the sensor/probe is preferably small to reduce any possible irritation that an adhesive may possibly cause on a subject's forehead.

Accordingly, the sensor or probes, 12 and 14, are designed to simultaneously and separately collect data from right and left hemispheres of a patient for comparison purposes which may be particularly useful should unilateral edema exist. In one contemplated embodiment for a device for edema monitoring and cerebral autoregulation assessment, the light sources are light emitting diodes (LEDs) that emit light waves at 730, 850 and 940 nm wavelengths to focus light absorption to deoxygenated hemoglobin (Hb), oxygenated hemoglobin ($HbO_2$) and water, respectively. By way of example, the light source 20 may include an Epitex LED capable of emitting light at wavelengths of 730 nm and 850 nm and a Roithner LaserTechnik LED cable of emitting light at 940 nm, and the photo detectors, 22 and 24, may be Burr-Brown silicon photodiodes having a 2.24 mm by 2.24 active area. Thus, the system 10 may enable changes in water concentration over time, changes in oxy-hemoglobin concentration over time, and changes in deoxy-hemoglobin concentration over time to be detected.

The control box 16 may host analog filters and amplifies and may be connected to a data acquisition board (DAQ) 34 which is connected to the computer 18. The DAQ 34 may be designed to be responsible for switching the light sources 20 and photo detectors, 22 and 24, which collect the reflected light. Thus, operation of the light sources at the three wavelengths may be controlled by data acquisition software on the DAQ 34 and powered by driving current.

The probes or sensors, 12 and 14, may house a thermistor to provide measurements on patient's temperature. These measurements may also be used in parameter adjustment for more reliable separation of Hb, HbO$_2$ and water content. By way of example, the thermistor may be a Digi-Key Part Number 615-1016-ND, US Sensor 103JG1J.

The temperature information may provide a safety mechanism for the device such that, if there is excessive skin heating caused by the device (e.g. due to a possible shortage or failure), the system 10 will automatically power off. The DAQ 34, control box 34, and/or unit 28 may have circuitry that collects data from the thermistor and causes the system 10 to power off when needed which can also be used for further parameter adjustment.

The light source for the NIR device uses light emitting diodes (LEDs) which provide a very compact wavelength light source. The LEDs provide highly monochromatic sources with very fast time sequencing (50 msec) and are available at 730, 850 and 940 nm. A power consumption of 0.2 watt, time shared at 1 msec is typical. No optical filter is necessary and detectors are circumferentially mounted (non-laser light).

The LEDs generate 0.016 Watt/cm$^2$ per second per wavelength. The three wavelengths are used individually, in a sequenced manner for about 1 msec each, i.e., the NIR system does not use multiple wavelengths at a given time. In addition, after each wavelength has been pulsed, there is an intermittent period when all three wavelengths are off before starting the next sequence. This intermittent period provides a benefit of allowing any heat generated by the LED to disperse. Therefore, the light intensity associated with any given length of exposure to the near infrared LEDs is less than the light intensity associated with an equivalent exposure to solar spectrum.

The maximum power of the system may be 5mWatt, there may be four measurement channels, data sampling rate may be 2 Hz to 1 kHz, and the main voltage may be provided by a medically graded power supply 110-220 VAC or 7.2 volt battery. Of course, these may be modified as needed. Accordingly, two light sources composed of three LEDs at 730, 850 and 940 nm wavelengths located on the contralateral sides of the sensors can be powered and data can be collected from four light detectors on the sensors.

Data Analysis

Since water has higher absorption around 940 nm as compared to other chromophores (oxyHb and deoxyHb), the light source 20 emitting light at a wavelength of about 940 nm focuses the attenuation of light primarily to changes in the concentration of water content in the brain. In addition, because the absorption of water and other chromophores such as melanin, lipid, hemoglobin, etc. are relatively small around 940 nm, light can penetrate tissue around this wavelength and a signal of sufficient strength can readily be detected by the photodetectors, 22 and 24, after light interacts with the tissue for reliable spectroscopic separation. The attenuation of light at the two other wavelengths, 730 nm and 850 nm, is for detecting changes in the concentration of the Hb and HbO$_2$, respectively. With the use of these three wavelengths together, spectroscopic measurements for the extraction of the primary chromophores of interest in the tissue such as water, oxyHb and deoxyHb can be performed.

Accordingly, changes in concentrations of water, oxyHb and deoxyHb due to edema can be reliably measured even in the presence of hemorrhage or hematoma which can occur simultaneously with edema or regardless of changes in the blood content due decrease in cerebral blood flow (CBF) or increased cerebral blood volume which are very common consequences of traumatic brain injury. Thus, the embodiment disclosed herein monitors both the hemoglobin and water contents in the brain.

The system 10 is designed to collect measurements from a patient over a period of time. During this time, regardless of edema development, changes in NIR measurements may occur due to signal drifts, temperature changes, cognitive activity, hematoma development, and the like.

Algorithms are provided to process the NIR measurements. The NIR system first measures optical density (OD) changes at the three wavelengths (730, 850 and 940 nm). By measuring optical density (OD) changes at three wavelengths where water, HbO$_2$ and Hb are the main absorbers, the relative change in water, Hb and HbO$_2$ versus time are obtained using the modified Beer-Lambert law (MBLL). If the intensity measurement at an initial time is $I_0$ (baseline), and at another time is I, the relative change in OD due to the variation in the concentrations of chromophores, $\Delta C_{water}$, $\Delta C_{Hb}$ and $\Delta C_{HbO2}$ during that period is found as:

$$\Delta OD^\lambda = -\log 10(I^\lambda/I_0^\lambda) = \varepsilon^\lambda_{Hb}\Delta C_{Hb} + \varepsilon^\lambda_{HbO2}\Delta C_{HbO2} + \varepsilon^\lambda_{Water}\Delta C_{Water})d\ DPF^\lambda$$

where d is the distance between light source and light detector, $DPF^\lambda$ is the wavelength dependent differential path length factor, $\varepsilon^\lambda_{Water}$, $\varepsilon^\lambda_{Hb}$ and $\varepsilon^\lambda_{HbO2}$ are the molar extinction coefficients of water, Hb and HbO$_2$, respectively. Measurements performed at three different wavelengths allow the calculation of $\Delta C_{water}$, $\Delta C_{Hb}$, and $\Delta C_{HbO2}$ solving the equation found by using the $\Delta OD^\lambda$ relationships:

$$\begin{bmatrix} \Delta C_{Hb} \\ \Delta C_{HbO2} \\ \Delta C_{Water} \end{bmatrix} = A^{-1} \begin{bmatrix} \Delta OD^{730nm} \\ \Delta OD^{850nm} \\ \Delta OD^{960nm} \end{bmatrix} \text{ where}$$

$$A = d \begin{bmatrix} DPF^{730}\varepsilon^{730}_{Hb} & DPF^{730}\varepsilon^{730}_{HbO2} & DPF^{730}\varepsilon^{730}_{Water} \\ DPF^{850}\varepsilon^{850}_{Hb} & DPF^{850}\varepsilon^{850}_{HbO2} & DPF^{850}\varepsilon^{850}_{Water} \\ DPF^{960}\varepsilon^{960}_{Hb} & DPF^{960}\varepsilon^{960}_{HbO2} & DPF^{960}\varepsilon^{960}_{Water} \end{bmatrix}$$

After traumatic brain injury or a hypoxic-ischemic event, edema and hematoma can develop separately or together at the same time or one after the other. In addition, when edema develops after brain injury, swelling in the brain can cause elevation of intracranial pressure and reduction of cerebral blood flow which can further change the blood oxygenation and cause hypoxia or ischemia. Regardless of such situation, since measurements will be obtained from the frontal cortex, any brain activity can cause changes in HbO$_2$ and Hb levels which can in turn affect signal levels. Hence, changes in blood content should be extracted and closely monitored together with the water content for the reliable and robust monitoring of edema. With the implementation of the light sources at three wavelengths, where each one is specifically selected to focus the light absorption to one chromophore (730 nm for Hb, 850 nm for $HbO_2$, and 940 nm for water absorption), water and blood content within the tissue can be effectively monitored.

The absorption spectrum of water, and also other chromophore such as $HbO_2$ and Hb, within the near infrared range changes related with change in temperature as shown in FIGS. 4-8. Temperature change can happen in patients with edema development or it can be a result of selected therapy like hypothermia. Since the system will be able to measure changes in the temperature by the use of the thermistor simultaneously with light attenuation, the signal processing component of the device will have the capability to automatically adjust the signal separation algorithm embedded in the system and use the temperature information to adjust the extinction coefficients in the MBLL accordingly for more reliable separation in Hb, $HbO_2$, and water content.

Figure 9:
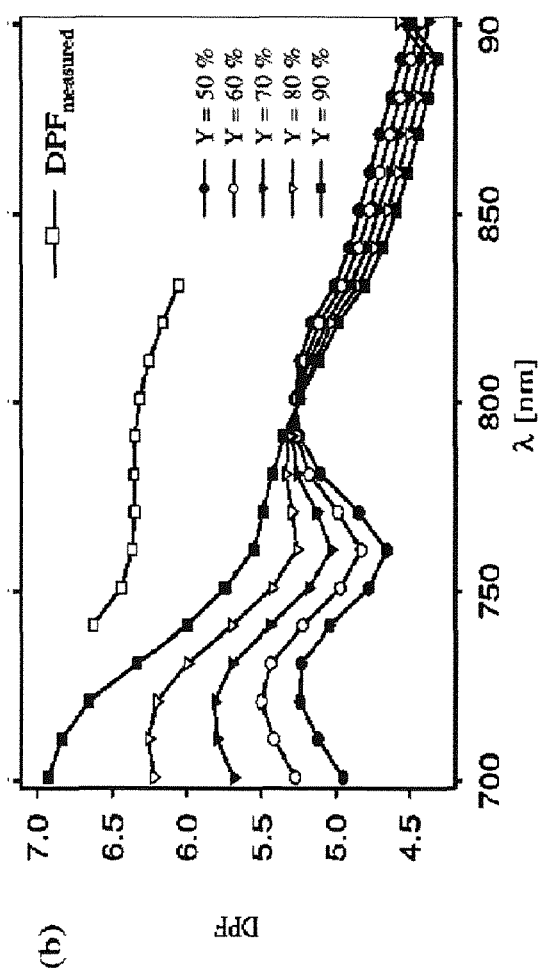
FIG. 9 is a graph showing changes in DPF relative to wavelength.

In addition, DPF changes, not only with wavelength, but also with source detector separation. For example, see FIG. 9. In the signal processing component of the device, appropriate DPF values will be embedded for different wavelengths and source detector separations in the MBLL algorithm. DPF further changes depending on variations in oxygen saturation. Hence, necessary adjustments are made to the DPF values when using it in MBLL for the reliable extraction of the chromophores by reducing crosstalk between measurements. Since the device can measure Hb and $HbO_2$ with the use of light sources at 730 and 850 nm wavelengths, it intrinsically has the capability of measuring local tissue oxygen saturation. Using the oxygen saturation measurements that can be obtained by the device, adjustments to DPF values can be established in the system for more reliable separation of water content from the remainder of the chromophores.

A common procedure in intensive care units is the repositioning of a patient during their prolonged stay in bed when they are unconscious in order to avoid bedsores. The patient population on which the system may be used may also primarily be critically ill patients who may be unconscious. Head movement and change in baseline measurements due to head movement, presents a problem for the NIR measurements. Even in patients that are awake, there can be head movement that can cause change in baseline values regardless of edema or hematoma development.

Thus, in addition to the above referenced parameter adjustments in the signal analysis component of the proposed device, the system will also have algorithms to identify and remove artifacts due to head movement or patient laying position adjustment by using the measurements obtained from contralateral sides (expected to be in reverse direction for artifacts), the timing and amount of change in the signal values (larger amount changes in shorter time as compared to changes that can be expected when there is edema or hematoma development). In such cases, when there is head movement or the laying position of a patient is changed (from back to right side or to left side) the baseline amount of blood and water will change accordingly (it will pool on the side that the patient is laying on or moved his/her head down to and move away from the other side). This type of signal change may be identified and corrected from the measurements. Certain markers can be put on the measurements at the time of patient repositioning which can be used in the identification of such signal changes. However, considering that medical personnel will be busy in taking care of patients, this type of marker placement can be missed and hence, an automatic manner for the identification of such baseline shifts may be utilized.

For example, one manner of automatically identifying head movement is by checking the rate and amount of change in the signal levels and comparing the right and left side measurements from the separate sensors. Edema or hematoma development is typically a slow process (minutes to hours) as compared to head movement or laying position change related differences in the measured signals (in seconds). The amount of change in the signal over a smaller period of time is also typically larger. Thresholds in signal level changes over time can be found and used to identify such regions.

Also, the change in the signal should be reverse in left and right side measurement when a repositioning happens. When laying position of the patient is moved from left side to right side (or back to right side or left to back side), blood should move away from the left side to the right side causing an increase in light absorption on the right and a decrease on the left. It will be reversed when the patient is moved from right to left side (right to backside or back to left side). Thus, there can be opposite changes in left side and right side channel measurements of the NIR system that can be used in the identification of baseline shifts due to head movement or patient repositioning.

One embodiment of a method of use of the NIR system or device described herein is for a method of assessing cerebral autoregulation in a mammalian subject. This method involves administering to the subject intravenously a composition comprising saline and an anesthetic; and obtaining multiple measurements from the subject over time of oxygenated (oxyHb), deoxygenated hemoglobin (deoxyHb) and water using near infrared spectroscopy (NIR). The multiple measurements obtained from the subject are evaluated against a reference standard to identify any change in the measurements of oxyHb, deoxyHb and water characteristic of hypoxic injury or aberrent cerebral autoregulation. As described above, such measurements may be obtained by use of an NIRS sensor in contact with the tissue of the forehead of the subject. The NIRS measurements are sequentially made within a single time period, i.e., are substantially simultaneous measurements of oxyHb, deoxyHb and water at each time point.

In certain embodiments, the method also involves obtaining from the subject baseline measurements of oxyHb, deoxyHb and water using NIR prior to administration of said composition; and correcting the additional measurements by subtracting the baseline measurements prior to analysis.

The composition infused into the subject during this method is generally an aqueous solution. Alternatively or in addition, the composition is accompanied by administration of an anesthetic or paralytic, either by the same or different routes. In one embodiment, the aqueous solution comprises normal saline solution. In another embodiment, the solution comprises sodium bicarbonate. In still another embodiment, the composition comprises a sugar, e.g., dextrose. In another embodiment, the composition contains an analgesic agent; and in a further embodiment, the analgesic agent is administered separately from the composition infused. Among useful analgesic agents is the analgesic agent Fentanyl or those mentioned herein. Other known analgesic agents may be selected by one of skill in the art with regard to this teaching. In still another embodiment the compositions comprises a paralytic agent; and in another embodiment, the paralytic agent is administered separately from the composition infused. Among useful paralytics is vecuronium. Other known paralytic agents may be selected by one of skill in the art with regard to this teaching. In other embodiments, the composition contains saline and an analgesic agent. In another embodiment, the composition contains saline and a paralytic agent. In still other embodiments, the composition comprises saline, an analgesic agent and a paralytic agent. One of skill in the art may select other components suitable for inclusion in to the composition.

As one example, a suitable composition comprises one or more of a concentration of 10 ml/kg weight saline, a concentration of 50 mcg/kg Fentanyl, and a concentration of vecuronium of about 0.1 mg/kg.

The composition is in one embodiment, administered at a rate of infusion of between 10 to about 20 ml/minute. Thus in certain embodiments, the infusion rate is 10, 11, 12, 13, 14, 15, 16, 17, 18, 19, 20 or more ml/minutes, including both endpoints and any fractional amount between the integers identified herein. The infusion of the composition generally occurs over a time period of about 1 to 2 minutes, including each endpoint and any fractional amount of the minutes therebetween. Other embodiments are also contemplated in which the infusion occurs over less than 60 seconds, e.g., down to about 10 seconds, or over a time period of greater than 2 minutes.

The volume of composition infused into the subject generally ranges from about 25 to about 40 ml, including both endpoints. Thus the infusion volume may be selected from 25, 26, 27, 28, 29, 30, 31, 32, 33, 34, 35, 36, 37, 38, 39, and 40 ml volumes, including both endpoints and any fractional amount between the integers identified herein.

The route of administration of the infusions may be selected from any known route found appropriate by a physician. In one embodiment, the administration route is intravenous. In another embodiment, the administration route is by inhalation.

It should be understood by one of skill in the art that following the teachings of this specification, a physician conducting this assessment may select the appropriate infusion rate, volume, route of administration and time period, as well as the components of the composition.

One particular example of the method involves administration of the composition comprising normal saline solution 10 ml/kg/dose rapid i.v. push over 1-2 minutes, 8.4% sodium bicarbonate solution 2 ml/kg/dose i.v. over 1-2 minutes, and 5% dextrose ½ normal saline solution i.v. 4-5 ml/kg/hr. Anesthesia was induced using inhalational isoflurane 4%, and maintained with nitrous oxide inhalational anesthetic 79-94% blended with oxygen FiO2 0.06-0.4 and adjusted to ensure proper depth of anesthesia and oxygentation. Adequate analgesia and sedation was ensured by giving additional doses of Fentanyl 50 mcg/kg/dose q 1-2 hours as needed. Paralytic agent vecuronium 0.1 mg/kg/dose (alternative: rocuronium) was administered q1-2 hours as needed to avoid any motion artifacts.

According to the above example of the method, the composition is administered intravenously for saline, dextrose, bicarbonate, analgesic and paralytic agents listed above, as intravenous route is the most effective route to achieve rapid plasma levels for intended effects. Anesthetic agents are administered by inhalational route.

The evaluation or analysis of the subject's NIR data is also part of the method for assessing cerebral autoregulation. This analysis involves evaluating and interpreting the subject's data at various timepoints against a selected reference standard. The selection of the reference standard is made by the physician to diagnose or identify the injury, its likely time or occurrence, and/or monitoring the subject's recovery from injury or response to treatment. The terms "Reference", "Reference Standard" or "Control" as used herein mean a level, standard or profile of reference NIR data e.g., OD or other signals detected by the NIR devices used in the methods described herein. To permit proper determination or identification of disease or injury based on the NIR measurements of oxyHb, deoxyHb and water, and optionally temperature, oxygen saturation or other data obtained from a subject, the subject's measurements are compared to reference.

In one embodiment, the reference standard is obtained from a reference human subject or population that is healthy and without any brain injury or disease. In one embodiment, the reference standard is obtained from a healthy reference human (or appropriate animal) subject or population that has not been infused with the saline and anesthetic composition used in some of the methods described herein. This reference human subject or population is a "normoxic" reference. In another embodiment, the normoxic reference standard is obtained from a healthy reference human subject or population that has been infused with the saline and anesthetic composition and has been monitored with NIRS measurements over identified periods of time before, during or after this infusion.

In still another embodiment, the reference standard is obtained from a reference human (or appropriate animal) subject or population that has had a hypoxic brain injury, edematous injury, or other brain injury event, i.e., a "hypoxic" reference. In one embodiment, this hypoxic reference subject or population has not been infused with the saline and anesthetic composition described herein. In another embodiment, the hypoxic reference standard subject or population has been infused with the saline and anesthetic composition and has been monitored with NIRS measurements over identified periods of time before, during or after this infusion.

In still another embodiment, the reference standard or control against which the tested subjects NIRS data is compared is a hypoxic reference subject or population which has been treated for hypoxic injury. This reference standard would be useful in monitoring the cerebral autoregulation of a patient undergoing treatment for a hypoxic injury. In still another embodiment, the reference standard is obtained the same subject undergoing testing and comprises the NIRS data from an earlier timepoint in testing. In another embodiment, the reference standard is a combination of two or more of the above reference standards.

In certain embodiments, the reference standard utilized is a standard or profile derived from a single reference subject. In other embodiments, the reference standard utilized is a standard or profile derived from averaged data from multiple reference subjects. The reference standard, in various embodiments, is a mean, an average, a numerical mean or range of numerical means, a numerical pattern, or a graphical pattern created from the NIRS data derived from a reference subject or reference population. Selection of the particular class of reference standards, or reference population depends upon the use to which the diagnostic/monitoring methods described herein are to be put by the physician.

Based on this evaluation and the relative changes in the subject's NIR data for oxyHb, deoxyHb and water compared to one or multiple reference standards, the physician can identify the occurrence of a hypoxic event or injury or disease in the subject by identifying a characteristic decrease in the NIR values occasioned by hypoxic injury. The same method is useful for monitoring and adjusting therapy for a subject recovering or under treatment for such a hypoxic injury.

EXAMPLES

The following examples are provided to demonstrate the effectiveness of the above referenced system and device and to demonstrate various methods of use. The examples include test results and methods performed on synthetic human brain-like phantoms, human adult patients having serious head injuries, and piglets.

Example 1

Synthetic Human Brain Like-Phantoms

Figure 10:
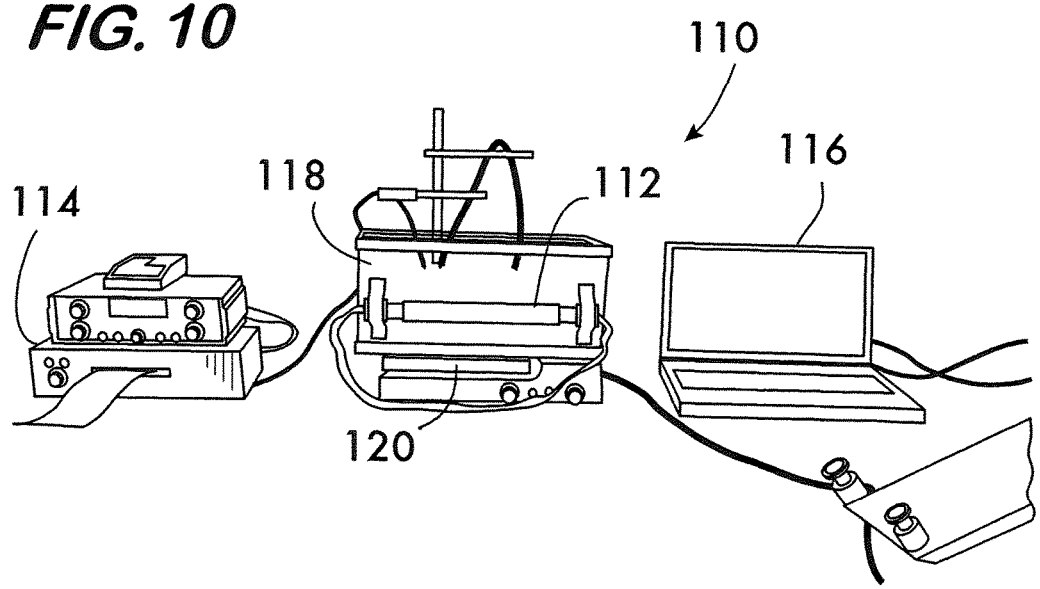
FIG. 10 is a perspective view of a clinical prototype edema monitoring system for laboratory testing using head mimicking phantoms according to an embodiment.
Figure 8:
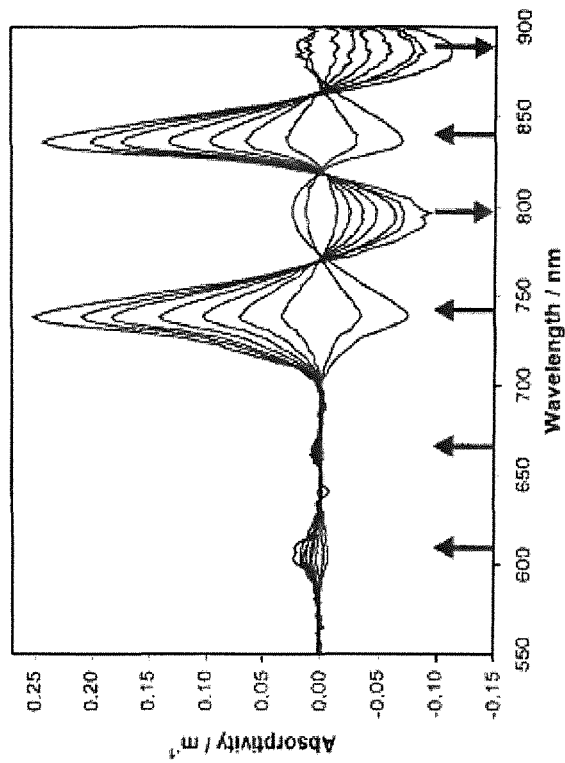
FIG. 8 is a graph showing a differential absorption spectrum of water over a temperature range of 15 to 60° C. with temperature increments of 5° C.
Figure 7:
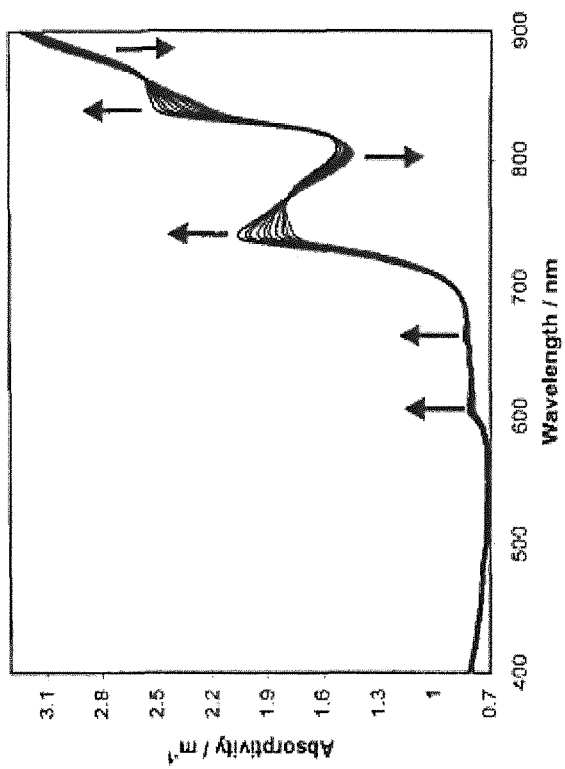
FIG. 7 is a graph showing an absorption spectrum of water over a temperature range of 15 to 60° C. with temperature increments of 5° C.

An overall edema monitoring system 110 according to an embodiment having a NIR sensor 112, data acquisition box 114, and presentation computer 116 is shown in FIG. 10 and was used during laboratory experimentation on a head mimicking phantom 118. This pre-clinical prototype is capable of measuring changes in water and blood content of the tissue within the head beneath the sensor collecting data on contra-lateral sides of the forehead at depth ~2 cm with a sampling rate of 2 Hz. In all the phantom tests reported here, the NIR sensor was used with light sources at 730, 850 and 960 nm wavelengths. A wavelength of 940 nm could be used in replace of the 960 nm wavelength and, in practice, has been found to provide a desired increase in measured signal strength.

The proposed system 110 was used to collect measurements over a period of time for monitoring purposes. During this time, regardless of edema development, changes in NIR measurements can occur due to signal drifts, temperature changes, cognitive activity, hematoma development, and the like. Some of these issues, such as the ones related with penetration, signal drift and temperature are discussed below in greater detail.

Penetration: The light sources in the NIR device 112 are driven sequentially and the light detectors collect light accordingly to generated data samples at each wavelength separately. In the data collection or aquistion box 114, all light sources were driven at the same current level that was specifically selected to guarantee penetration and eliminate the possibility of saturation at 730 and 850 nm wavelengths. With the addition of another light source at 960 nm wavelength, it was necessary to first make sure that there was no saturation and enough penetration if light source at 960 nm is driven with the same current as the others.

The signal levels at 960 nm are first tested for saturation and penetration on human head mimicking phantom 118 before performing any further phantom tests on edema detection and monitoring. It is usually impractical to switch the driving current back and forth for different light sources during sequential data collection at different wavelengths. Instead it is preferred to use the same driving current for each light source and adjust the signal level accordingly by using optical filters on detectors to eliminate saturation or to use multiple light sources at same wavelength to increase signal level which will ensure penetration. The signal levels of the prototype NIR sensor 112 are tested and adjusted on the multi-layer liquid phantom 118 with optical and physical characteristics mimicking an average adult human head with absorption and scattering coefficients selected as $\mu_a=0.05$ $cm^{-1}$ and $\mu_s=10$ $cm^{-1}$ respectively as published in literature. The tests suggested the use of two 960 nm light sources together to ensure penetration at this wavelength and to eliminate saturation. Alternatively, a single 940 nm light source can be used instead of multiple 960 nm light sources.

Signal Drift: Prolonged NIR measurements on the fixed phantom 118 of certain optical and physical properties are carried out to detect the amount of signal drifts over time due to electronics and optical components. Human head models were built using the multi-layer liquid phantom with optical properties of an average adult with $\mu_a=0.05$ $cm^{-1}$ and $\mu_s=10$ $cm^{-1}$ as published in the literature. NIR measurements were continuously collected over several hours using the NIR system 110. The drift test was performed three times where the first test was for 2 hours, the second was for 3 hours and the last test was for a 6 hour period. Each time the phantom was rebuilt, it was rebuilt with similar optical and physical properties as explained above.

The light intensity measurements at 730, 850 and 960 nm wavelengths during the 6 hour period test are shown in FIG. 11. The mean of the maximum change or drift in the intensity after the signal reaches steady state (±standard deviation) over three drift tests is found as 0.7±0.4% for 730 nm, 0.5±0.3% for 850 nm and 0.1±0.03% for 960 nm. The mean±standard deviation of the slope of the time course of the recordings using the three drift tests are found as $(3.4\pm4.2)\times10^4$ for 730 nm, $(5.2\pm3.5)\times10^{-4}$ for 850 nm and $(2.1\pm0.9)\times10^{-4}$ for 960 nm. The change in the signal due to drift are of several orders of magnitude less than the change in the signal due to edema development as was found in phantom tests for edema development (20-to-40% change in the NIR signal intensity for a 1-to-3% increase in the water content in the brain). Hence, signal drift in the embodiments of a NIR system, as disclosed herein, will not generate a significant amount of change in the signal levels that would otherwise confound decisions regarding edema.

There is a transient period until the NIR signal reaches its steady state value in the beginning 3 to 5 seconds of the experiment after the light sources are powered for the first time. In FIG. 12, the first 50 seconds of raw intensity measurements are shown for 6 hour test and 3 hour test, respectively. As can be seen, there is a transient period in the first 3 to 5 seconds of recording until the signal reaches its steady state value which stays at the same level relatively constantly in the following time intervals. The transient period can be eliminated by discarding the first 10 seconds of measurements within each recording.

Figure 14:
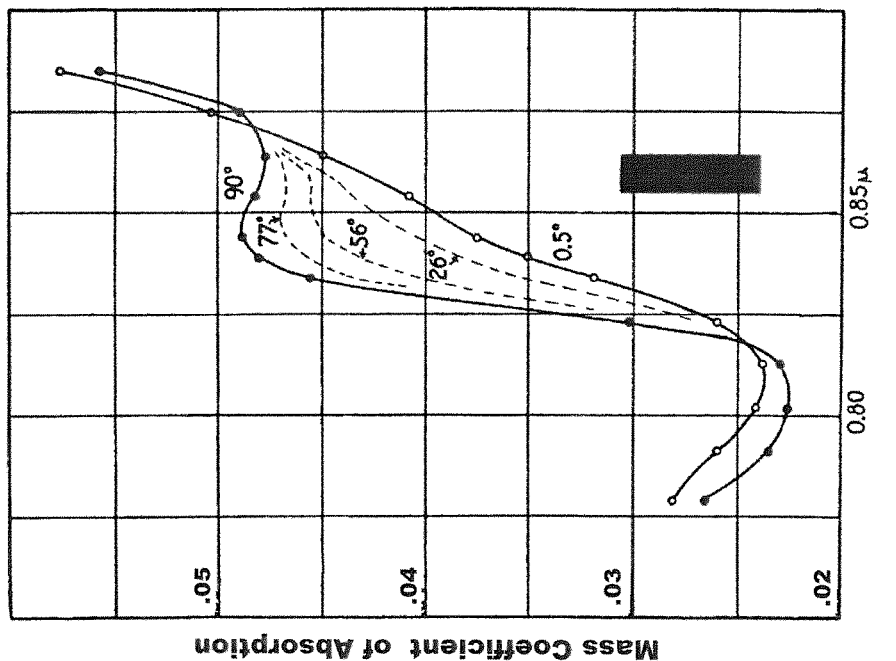
FIG. 14 is a graph representing changes in the absorption spectrum of water due to changes in temperature from 0.5° C. to 90° C. at around 850 nm.
Figure 13:
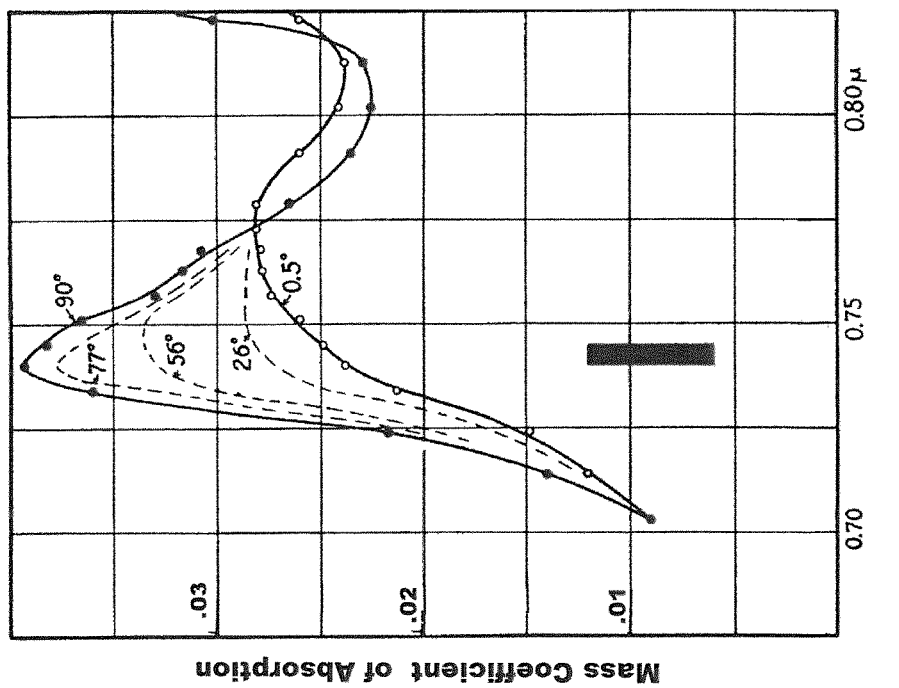
FIG. 13 is a graph representing changes in the absorption spectrum of water due to changes in temperature from 0.5° C. to 90° C. at around 730 nm.
Figure 15:
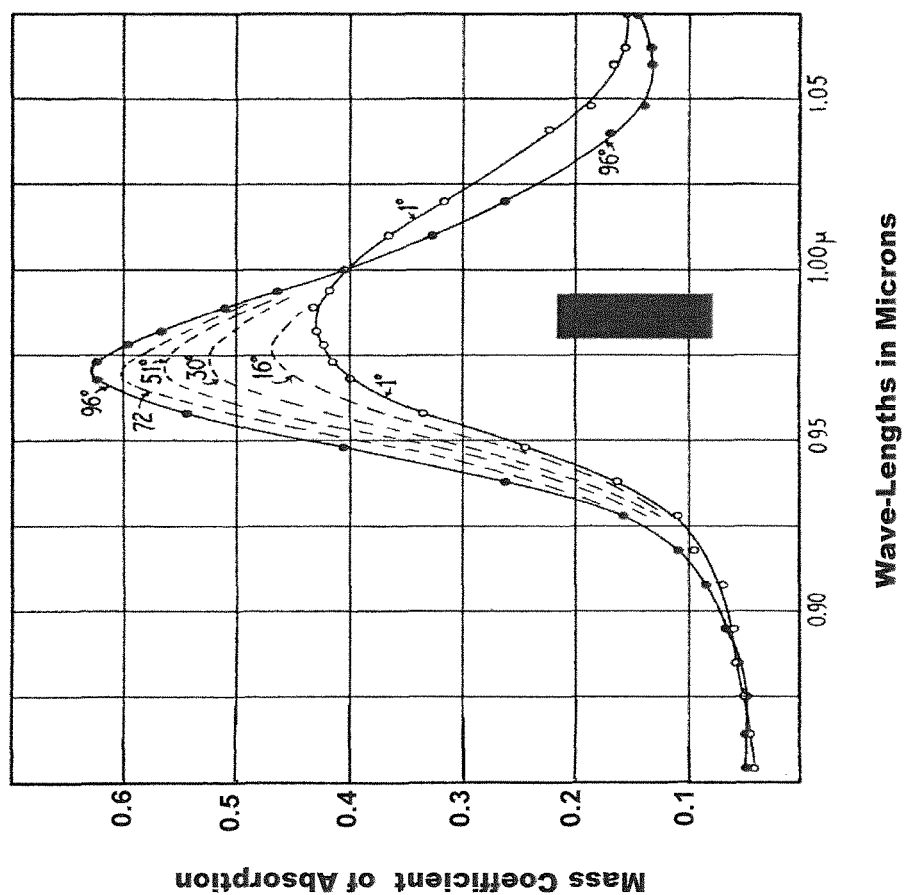
FIG. 15 is a graph representing changes in the absorption spectrum of water due to changes in temperature from 0.5° C. to 90° C. at around 960 nm.

Temperature: The absorption of water at different wavelengths is highly dependent on temperature changes. In fact, absorption of Hb and $HbO_2$ also slightly changes with temperature. The changes in the absorption coefficient of water at different wavelengths have been previously reported, for instance, as shown in FIGS. 13-15. As can be seen at around 730, 850 and 960 nm (the wavelengths that were used in the NIR sensor 112), there is a large change in the absorption of water due to changes in temperature from 0.5° C. to 90° C. Changes in absorption of water due to temperature is especially important in studies involving edema since patients who developed edema can also experience changes in their temperature. Such changes related with temperature are also observed in Hb and $HbO_2$.

Figure 16:
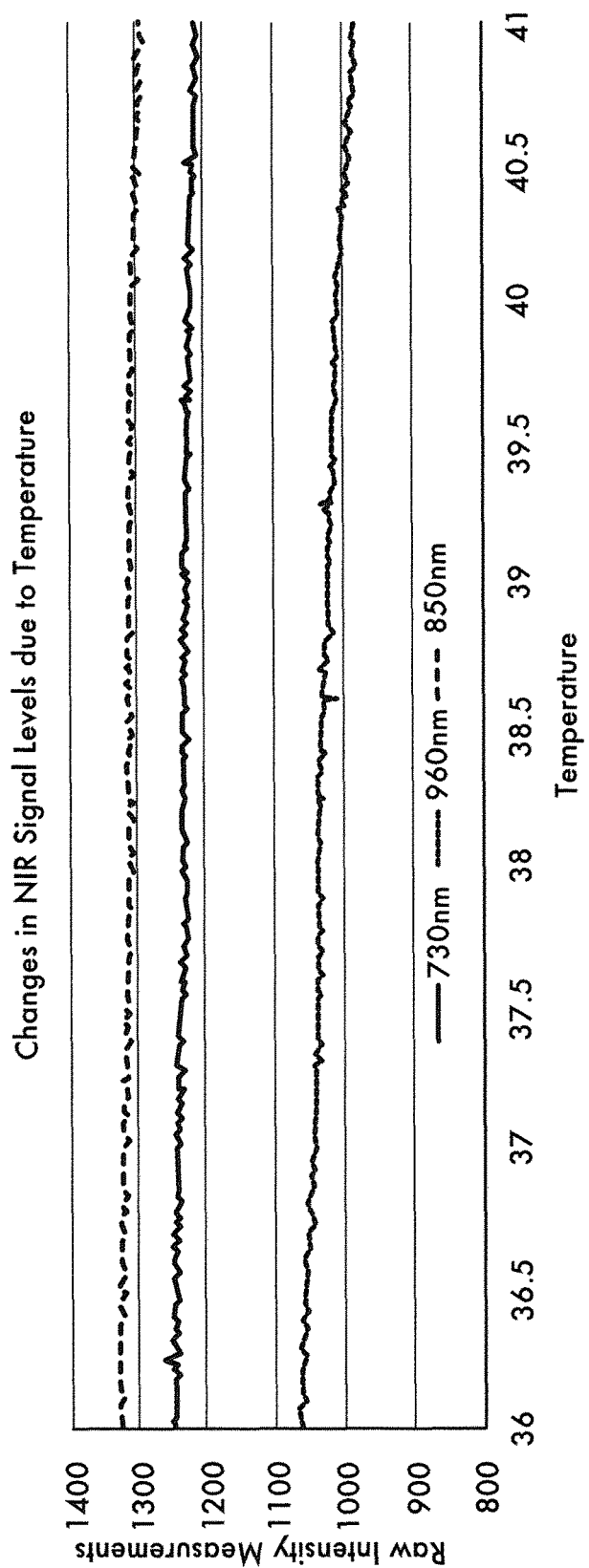
FIG. 16 is a graph representing changes in NIR intensity levels at 730, 850 and 960 nm wavelengths due to changes in temperature between 36° C. and 41° C.

The change in the NIR signal was studied at different wavelengths due to changes in temperature. A temperature test was performed on the multi-layer liquid head phantom 118 as in the signal drift studies with the same optical and physical characteristics mimicking an average adult human head. The brain compartment of the phantom 118 is placed over a heater 120 and the temperature of the liquid within the brain layer was increased linearly from ambient temperature 24° C. to 42° C. over time. A magnetic stirrer was on during the course of the experiment to keep the temperature of the liquid mixture in the brain compartment homogeneous. Since experiments will be carried out on humans, primarily of interest is the amount of change in the signal for temperatures between 36° C. to at most 41° C. The raw NIR intensity measurements at 730, 850 and 960 nm wavelengths versus the temperatures between 36° C. to 41° C. are shown in FIG. 16. When the temperature increases, absorption coefficient of water increases and hence detected light intensity decreases at all wavelengths used even though the concentrations of water and other absorbers within the phantom 118 remain constant. In the measurements, the change in the signal levels between the temperature region of interest (between 36° C. and 41° C.) is around 4.2% for 730 nm, 3.8% for 850 nm and 10% for 960 nm. These percent levels of change in the NIR signals are comparable to signal level changes (20-to-40%) due to 1-3% change in the water content of the brain as measured by phantom tests for edema monitoring. Therefore, it is important to pay attention to changes in the patient's temperature in order to use correct absorption parameters in the extraction of water content within the brain to detect and monitor edema development. The device with built in temperature measurement capability can automatically adapt the parameters in MBLL for more reliable signal separation.

Phantom Tests for stability and reliability: The system 110 may be used in a continuous fashion or in an on-off type fashion where it can be powered on and collect data and be powered off for a period of time in between data collection sessions. A test of the performance of the system 110 on solid and liquid phantoms in Willis of stability and reliability during continuous and on-off type of measurements was performed. In real human subject testing, all the changes in the measurements can be obtained continuously, every hour or in 6 hour intervals will be calculated relative to the first measurement period. Accordingly, the system 118 was tested for capability of providing the same measurement levels in a stable fashion in a next measurement period after the device was powered off and then powered back on again as compared to the previous data collection period given that there was no change in the water and blood content in the medium.

Figure 17:
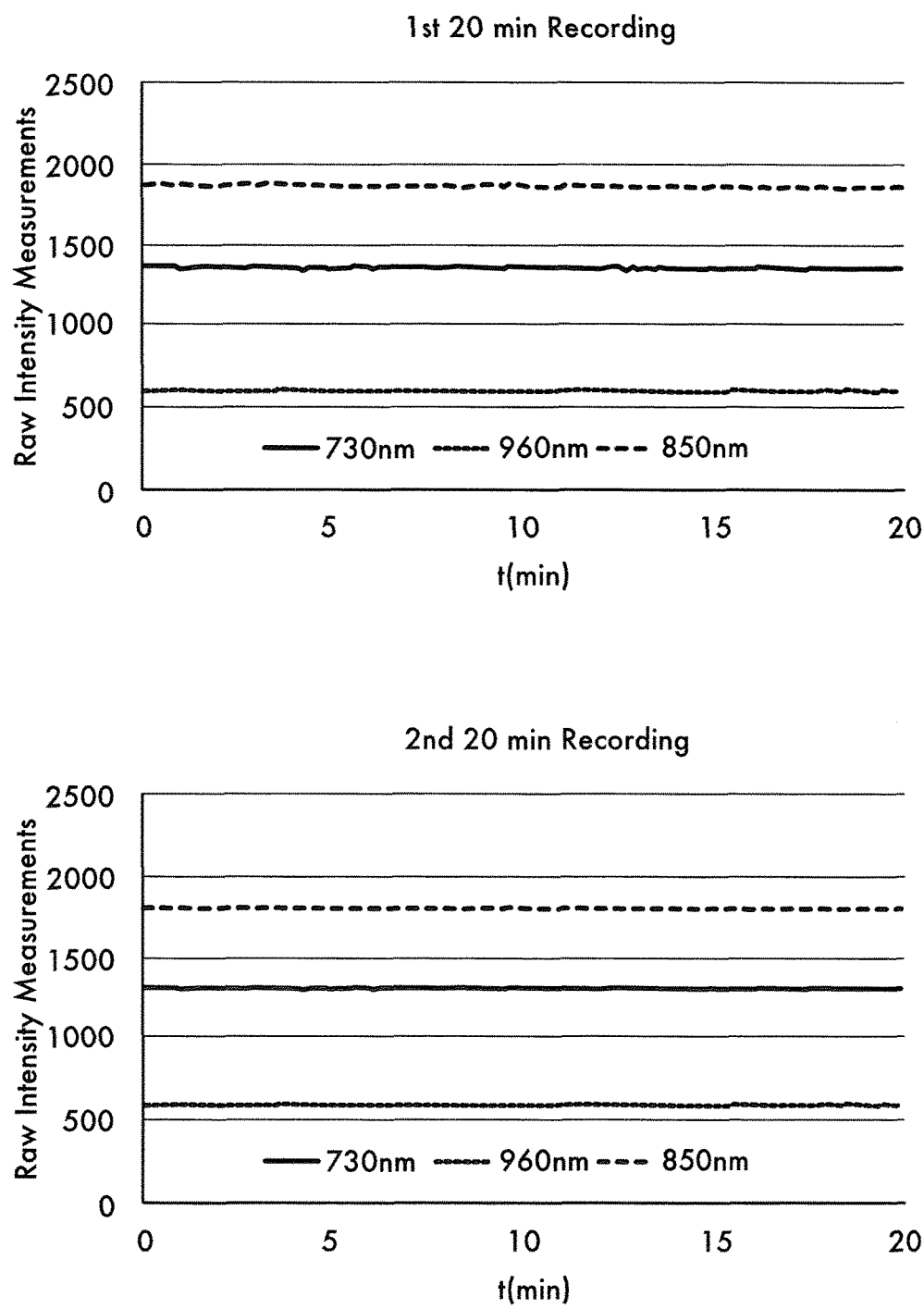
FIG. 17 is a graph representing results of four consecutive measurements of 20 minutes every 3 hours on a liquid phantom without (first graph) and with diffuse edema (last graph) where edema is introduced in between 2nd and 3rd set of recordings (the signal levels change in the measurements in the first and fourth graphs due to diffuse edema).
Figure 17:
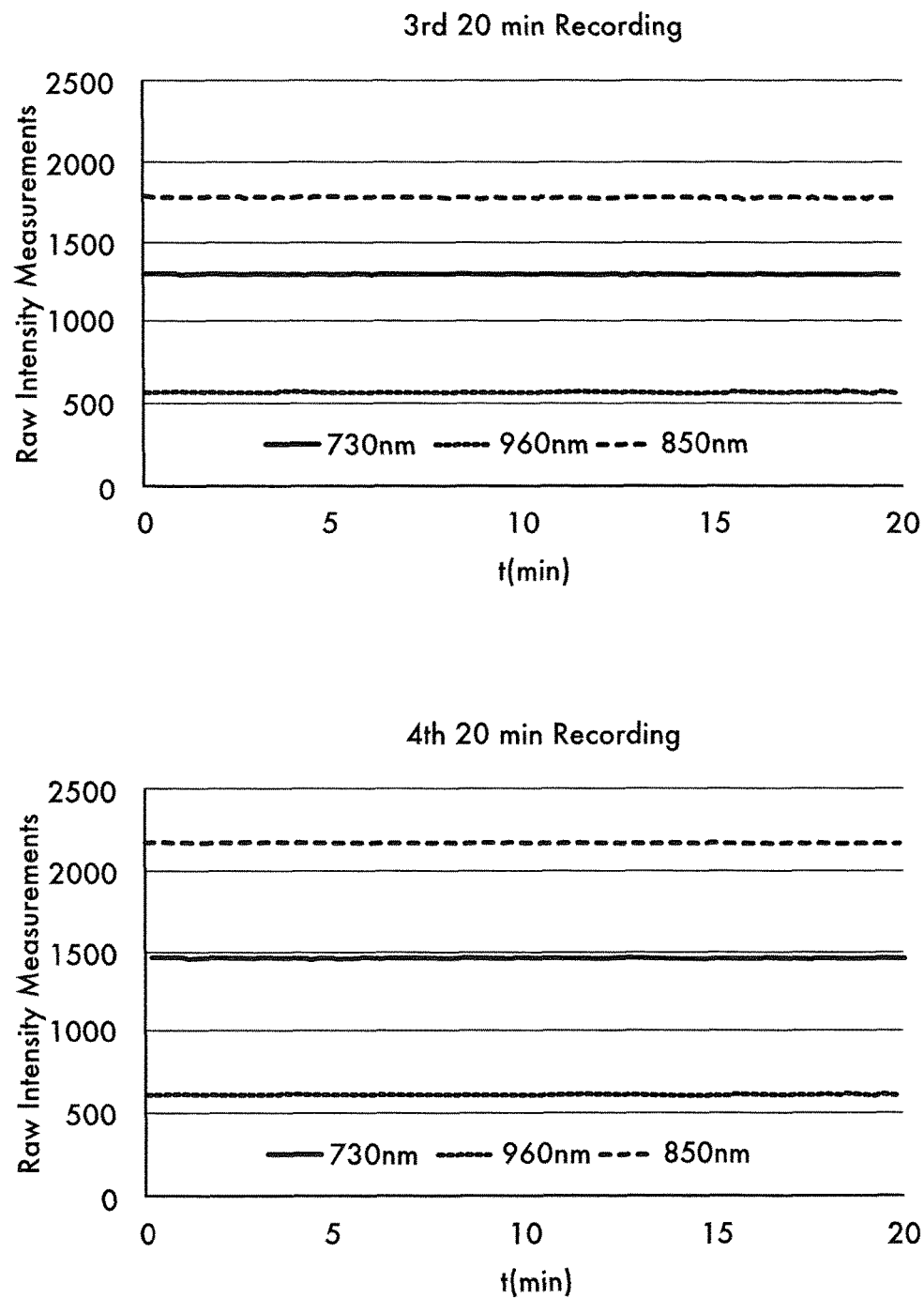

For this purpose, two tests were performed. In a first set of experiments to test the stability and reliability, the liquid phantom 118 was used. Recordings of 20 minutes were obtained every 3 hours for four times. In the first two sets of recordings, the water content in the brain layer of the phantom 118 was the same. Between the 2nd and 3rd set of recordings, the water content was changed by adding water to the brain layer of the phantom 118 to mimic diffuse edema. In the last 2 sets of recordings, the measurements obtained are when the same diffuse edema was present. The results of this test are presented in FIG. 17. It was observed from the results of these tests that the edema monitoring device 118 provides stable measurements when there is no change in the water content of the brain. The change in the levels of raw intensity measurements is negligible when the device records continuously and also after it is turned off and back on again. The device is also capable of reflecting the changes in the water content repeatedly and reliably when it is present.

Figure 18:
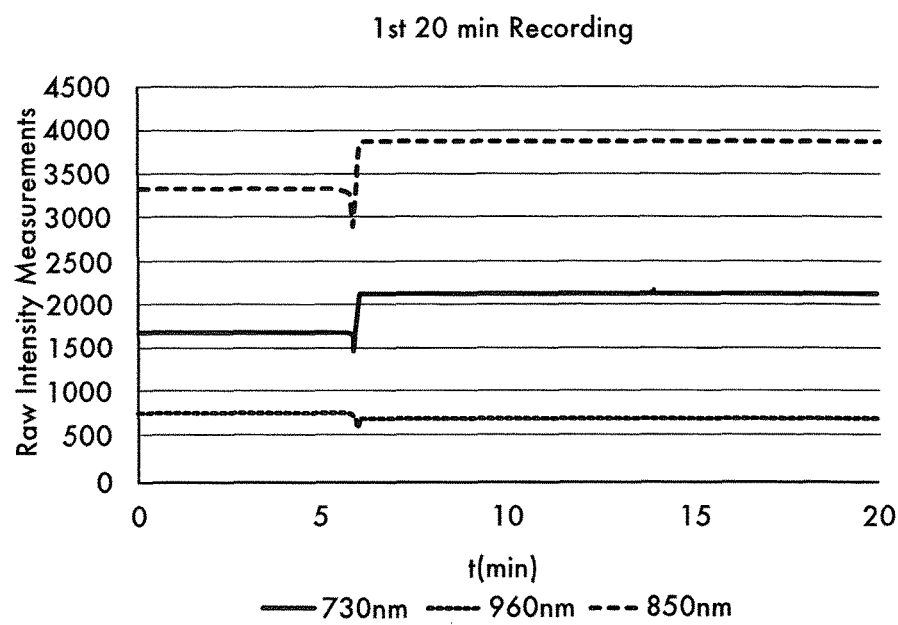
FIG. 18 is a graph representing the results of a first of two consecutive measurements of 20 minutes within 3 hours on a solid phantom without edema (beginning of the figure) and with edema (introduced ~5 min in the figure where signal levels change and remain the same over time).
Figure 19:
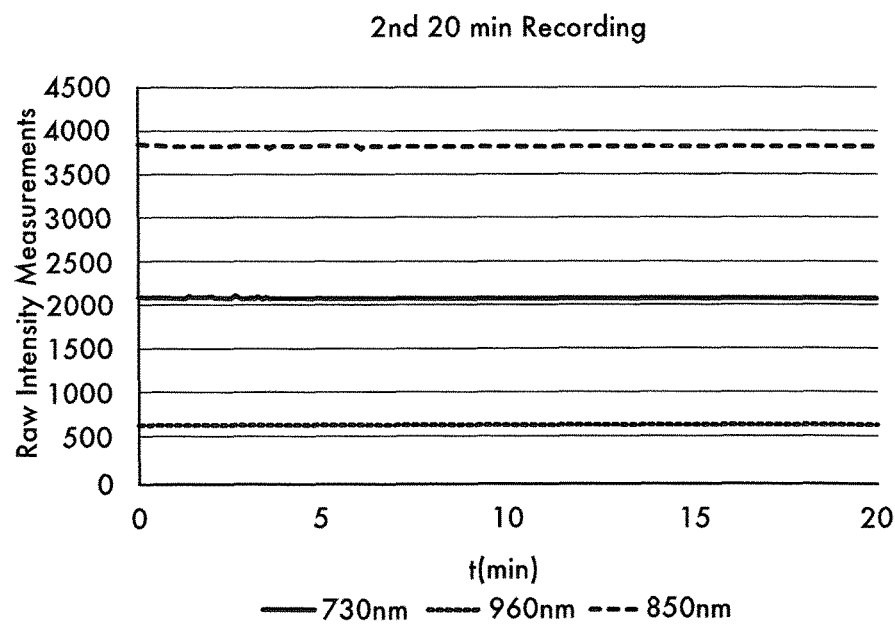
FIG. 19 is a graph representing the results of a second of two consecutive measurements of 20 minutes within 3 hours on a solid phantom with edema (signal levels remain the same over time).

In a second set of experiments, a solid phantom was used with a hole drilled on one side. In the first recording period of 20 minutes, the sensor was placed on a solid side of the phantom that mimics the optical properties of a normal adult human head. After 5 minutes, the sensor was moved on the hole side that was filled with water mimicking focal edema. This first recording is shown in FIG. 18. When the sensor recorded from the water filled area, since the optical properties of the medium changed, the values in the raw intensity measurements have changed after 5 minutes of recording. Then, the device was powered off and after 3 hours was re-started to collect measurements for 20 minutes from the same location where focal edema model existed. These recordings are shown in FIG. 19. In this second set of measurements where the sensor was located on the focal edema location, it was observed that the levels of raw intensity measurements started from the same values as they were in the last portion of the first set of measurements obtained 3 hours before and stayed the same for the whole 20 minute period as would be expected since no change in the water content was introduced.

Example 2

Testing and Evaluation of the Performance of the Clinical Prototype Device in Edema and Hematoma Detection Using Laboratory Tests Under Different Oxygen Saturation Conditions Several phantom tests were performed using laboratory prototype device measurements and the performance of the device and the analysis algorithms in the separation of water and blood content under different oxygen saturation conditions were evaluated. The results of these tests were used not only for the evaluation of the performance of the NIR system with 730, 850 and 960 nm wavelength light sources and algorithms based on MBLL in edema detection and monitoring but also for the identification of necessary adjustments required to improve their performance. The tests justified the use of MBLL in resolving Hb, $HbO_2$ and water concentrations and the selection of 960 nm wavelength light source to focus the measurements to the water content of the brain. A 940 nm wavelength light source may also be utilized in place of the 960 nm wavelength light source.

The following measurements and the results of the NIR data analysis are used for the validation and evaluation of the performance of the embodiments of an edema monitoring system and data collection procedures disclosed herein. In these experiments, focal and diffuse edema or hematoma development and changes in oxygen saturation was modeled.

Phantom Preparation and Experimental Design: Different scenarios were modeled that could happen after traumatic brain injury or a hypoxic event on laboratory phantoms involving different types of edema development in the presence and absence of hematoma and blood oxygenation changes. In all of the experiments used in this study, liquid phantom simulating the optical properties of an adult human head was used.

The basis of the phantom is formed by a scattering solution of Intralipid and phosphate buffered saline with pH=7.4. Certain concentration of Intralipid and water is mixed until a typical overall reduced scattering coefficient of brain is reached. The solution is placed in the brain layer of the liquid head phantom which is a cubic container of approximately 10 cm on each side with a magnetic rod that stirred the solution during the course of the experiments. Red blood cells obtained from healthy sheep blood was added to the intralipid solution that contained no hemoglobin at the start of the experiment to achieve a volume fraction of 1.5% and total hemoglobin concentration of 24 μM. This is a typical value for normal physiological conditions with an assumption of 4% blood volume and 40% hematocrit. The hemoglobin saturation in the added red blood cells was adjusted to ~90%. In order to change oxygen saturation and to induce deoxygenation, baker's yeast was added to the solution obtained as explained above. The temperature of the phantom was maintained at 37° C. to keep the yeast active. This condition is maintained over the time course until deoxygenation of yeast-intralipid solution reaches steady state. Then oxygenation is induced again by delivering extra oxygen to the liquid phantom from an oxygen tank. Oxygen supply is maintained until a steady state level of oxygenation is obtained.

(Experiment I) Edema development under different Oxygen Saturation conditions: When edema develops after brain injury or a hypoxic event, swelling in the brain can cause elevation of intracranial pressure and reduction of cerebral blood flow which can further change the blood oxygenation and cause further hypoxia or ischemia. Regardless of such a situation, since measurements will be obtained from the frontal cortex, any brain activity can cause changes in $HbO_2$ and Hb levels which can in turn affect signal levels. Hence, changes in blood content should be extracted and closely monitored together with the water content for the reliable and robust monitoring of edema.

In this experiment, the water content through diffuse and focal edema models in the presence of changes in the blood oxygenation was changed. The algorithms and the parameters used in the algorithms are adjusted to provide more reliable and robust measurements. In these experiments, the performance of the prototype edema monitoring system 110 with a thin strip NIR sensor 112 composed of light sources at 730, 850 and 940/960 nm wavelengths and the data acquisition box 114 was evaluated. The device and the analysis methods based on MBLL are tested in the separation of blood and water content under different blood oxygenation conditions.

Diffuse Edema Tests: In these experiments the oxygenation of intralipid+blood+water solution in the brain layer of the phantom is first adjusted to ~90% saturation and then yeast is added to induce deoxygenation. Once deoxygenation reached steady state around ~10% blood oxygenation is increased once more by introducing oxygen to the solution until saturation reached steady state at ~90%. Diffuse edema model is simulated by adding a certain percentage of water (10%) to the brain layer solution at different blood oxygenation conditions (~90%, ~50% and ~10% oxygen saturation).

Figure 20:
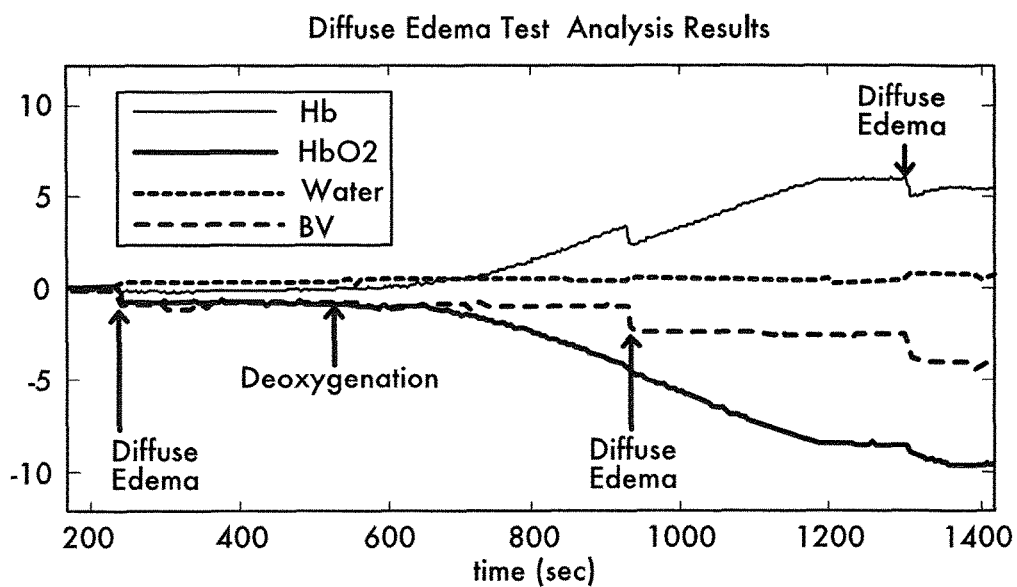
FIG. 20 is a graph representing diffuse edema results of MBLL for Hb, $HbO_2$, water and Hbt at 3 cm source detector separation where 10% water was added at ~90%, ~50% and ~10% saturation condition.

In FIG. 20, the results of MBLL providing relative changes in water, Hb and $HbO_2$ concentrations according to the first 10 second recording at the start of the experiment using the raw intensity measurements at 730, 850 and 960 nm wavelengths of the NIR device are shown. During the course of the experiment 10% water is added to the base solution at ~90%, ~50% and ~10% oxygen saturation conditions. Each time after the water is added to the solution, the concentration of water increases and concentrations of Hb, $HbO_2$ and Hbt (blood volume or total hemoglobin Hbt=Hb+$HbO_2$) decreases since they become diluted. When the yeast is added to the solution it induces deoxygenation and hence Hb increases while $HbO_2$ decreases. During this process Hbt and water concentrations remain relatively constant as expected. The water, Hb and $HbO_2$ concentration changes as measured by with 730, 850 and 940/960 nm wavelengths completely followed expected patterns in this experiment.

Figure 21:
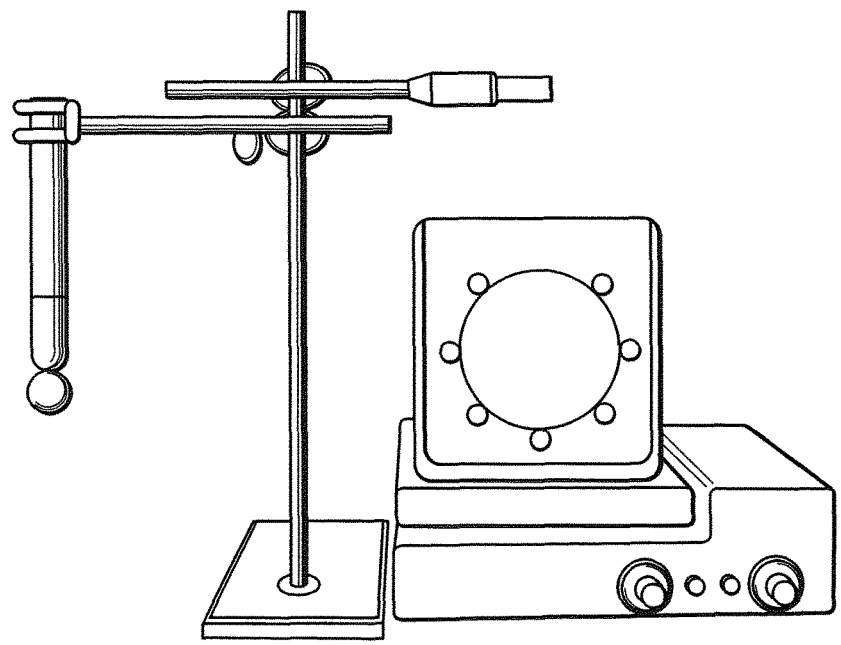
FIG. 21 is a perspective view of laboratory equipment used during focal edema tests according to an embodiment.

Focal Edema Tests: In these experiments, the same procedure is applied to induce oxygenation and deoxygenation as in the diffuse edema model tests. Here focal edema is simulated by inserting a rubber balloon filled with water to mimic edema of size 20 cc in the intralipid+blood+water solution in the brain layer of the phantom as shown in FIG. 21.

Figure 22:
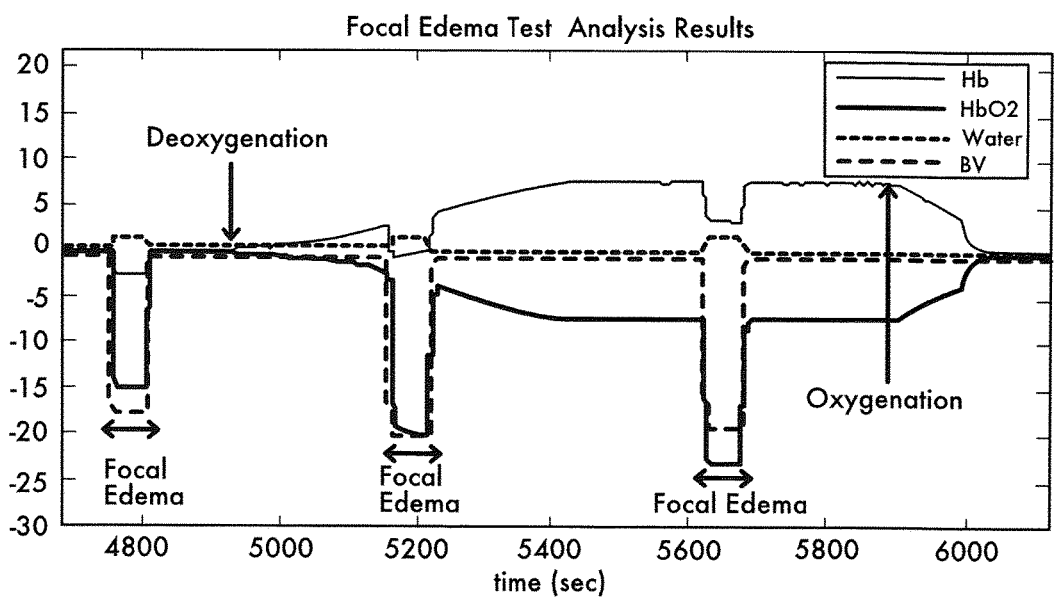
FIG. 22 is a graph representing focal edema results after MBLL for Hb, $HbO_2$, water and Hbt at 3 cm source detector separation where 20 cc volume water balloon was inserted at ~90%, ~50% and ~10% oxygen saturation conditions obtained using light sources at 730, 850 and 960 nm.

Results of MBLL as the relative changes in water, Hb, $HbO_2$ and Hbt concentrations using the prototype edema monitoring device measurements are shown in FIG. 22. In this experiment, 20 cc volume focal edema was inserted and taken out at ~90%, ~50% and ~10% oxygen saturation conditions.

In these focal edema experiments, when the focal edema model is inserted within the brain layer independent of the oxygen saturation the measured water concentration increases, as expected. Since the blood concentration becomes diluted, Hb, $HbO_2$ and Hbt decrease during the focal edema condition. These expected results are captured with the edema monitoring device with the use of the light source at 960 nm wavelength (a 940 nm light source may also be used).

Figure 23:
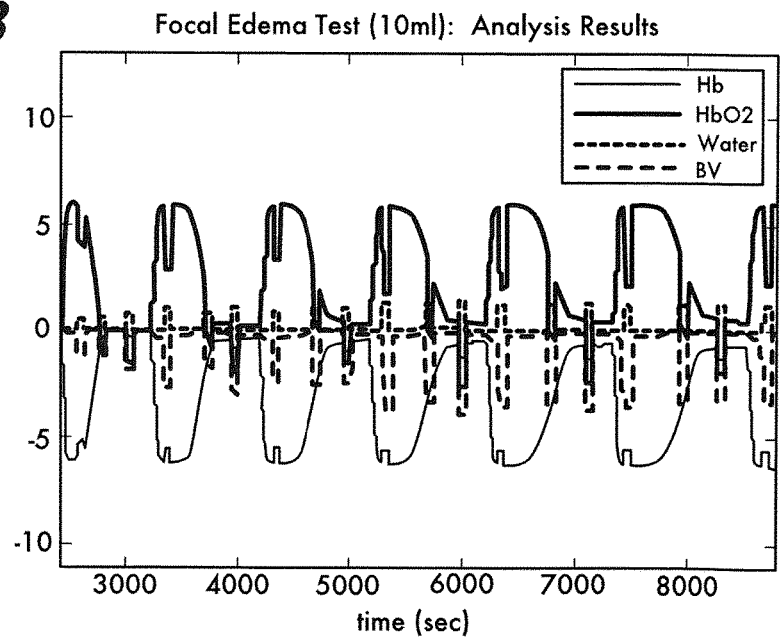
FIG. 23 is a graph representing focal edema test results when a water balloon filled with 10 ml of water is dipped in and taken out of the brain region of the phantom repeatedly for <10%, ~50% and >90% oxygen saturation conditions.
Figure 24:
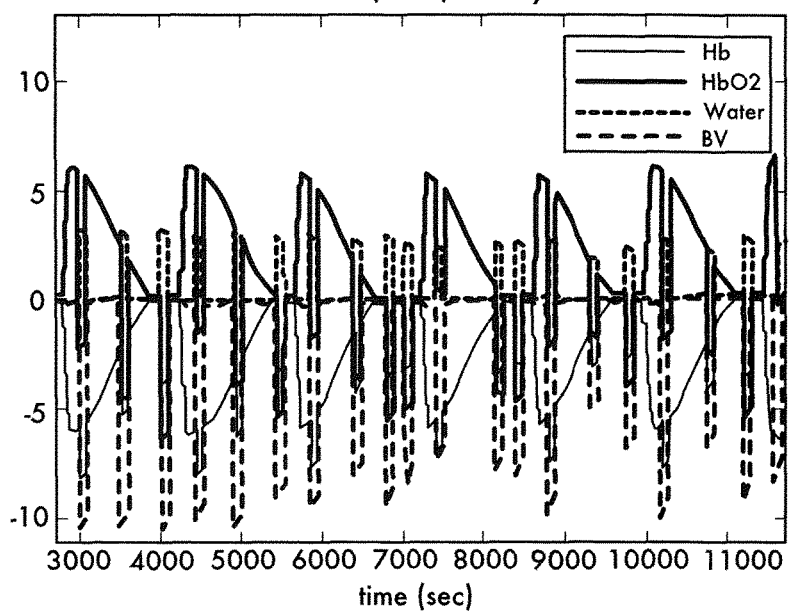
FIG. 24 is a graph representing focal edema test results when a water balloon filled with 30 ml of water is dipped in and taken out of the brain region of the phantom repeatedly for <10%, ~50% and >90% oxygen saturation conditions.

The focal and diffuse edema tests were repeated several times. The same results were obtained in the repeated trials when the change in water content (edema size) is kept the same. When change in water content is increased from focal edema of 10 ml (see FIG. 23) to 30 ml (see FIG. 24), the measurements obtained by the proposed edema monitoring device reflect the change successfully and repeatedly. In the case of 10 ml focal edema change, water content was ~1 μmol, where as in the case of 30 ml focal edema, it was ~2.5 μmol.

(Experiment II) Hematoma tests under different Oxygenation Saturation conditions: After traumatic brain injury, edema and hematoma can develop separately or together at the same time or one after the other. In this experiment, the development of hematoma without the presence of edema was modeled and the performance of the prototype device and the analysis techniques in the separation of blood and water content was tested. Here, hematoma is simulated by inserting a rubber balloon filled with 20 cc volume of red blood cells using a stable holder in an intralipid+blood+water solution in the brain layer of the phantom similar to the focal edema model.

Figure 25:
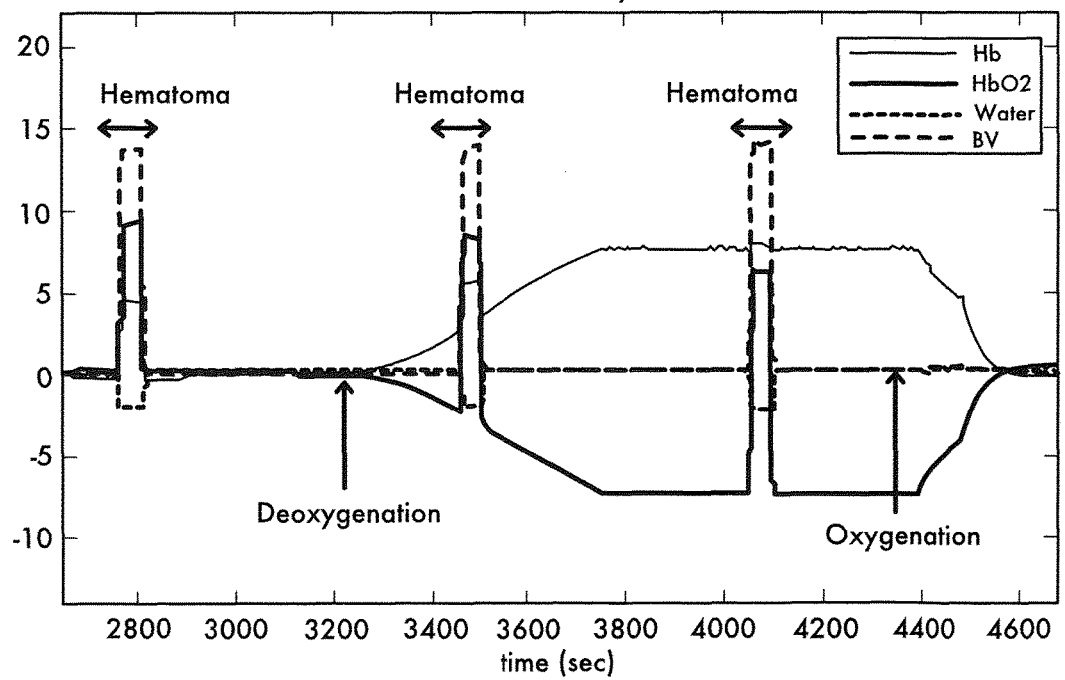
FIG. 25 is a graph representing hematoma model results after MBLL for Hb, $HbO_2$, water and Hbt at 3 cm source detector separation where 20 cc volume rubber balloon filled with blood was inserted at ~90%, ~50% and ~10% oxygen saturation conditions.

FIG. 25 shows the relative changes in water, Hb, $HbO_2$ and Hbt concentration for 20 cc hematoma test obtained. As in focal edema experiments, the hematoma model is inserted during ~90%, ~50% and ~10% oxygen saturation conditions. In all of the blood oxygenation conditions, Hbt concentration increases with the insertion of the hematoma as expected. Change in Hb and $HbO_2$ depends on the oxygen saturation of the blood within the balloon and within the brain layer solution outside the balloon. The water content was expected to drop a little bit as was the case in most of the oxygen saturation conditions.

Example 3

Human Testing

A study was performed with severe head trauma patients of ages between 18-65 admitted to an intensive care unit (ICU) and confirmed with edema development through computed tomography (CT) scanning. The NIR sensor is attached on the patient's forehead with a hypoallergenic medical grade adhesive tape. Measurements from the NIR sensor attached to the patients' frontal scalp are taken serially for 10-20 minutes every 6 hours for a total of 72 hours period following the onset of first measurement. The sensor was not removed until all the measurements are collected within the 72 hours period following the initial measurement in order to avoid the possibility of placing the sensor on a different location on the forehead with different optical properties. The sensor remained attached but is powered off when it is not recording in order to eliminate unnecessary application of light and heating to the forehead. Serial data collection over a period of time is necessary in order to be able to monitor possible changes in edema development. In addition to NIR measurements, patients' neurological status obtained through Glasgow coma scale (GCS) scores, intracranial pressure monitoring (ICP) and CT or magnetic resonance imaging (MRI) scans were also obtained serially for correlation analysis to validate the efficacy of NIR technology in edema monitoring. A thin strip NIR sensor with light sources at 730, 850 and 960 nm wavelength was used.

Patient 1: A first patient was a 48 year old white male who had two gunshot wounds to the head. The edema monitoring device used in this study was composed of: i) a thin strip sensor housing LED type near infrared (NIR) light sources at three wavelengths at 730, 850 and 960 nm and light detectors; ii) a data acquisition box to power the light sources and to collect data from the light detectors; and iii) a laptop computer for data collection and storage.

The edema monitoring sensor was placed on the patient's forehead with a cushioning material for comfort and a hypoallergenic medical grade adhesive tape to hold the sensor in place during the course of data collection. Data collection recorded measurements from the edema monitoring sensor at 2 Hz from the contra-lateral sides of the forehead at depth ~2 cm serially for 20 minutes every 6 hours in 3 days period following the onset of first measurement by automatically turning the device on and off. Once the data from the edema monitoring device was finalized, the sensor was detached. Other neurological and physiological measurements such as Glasgow coma scale (GCS) scores, intracranial pressure (ICP) monitoring recordings and computed tomography (CT) scan results recorded at the same day and time points on the patient were obtained for performance evaluation of the device.

Figure 26:
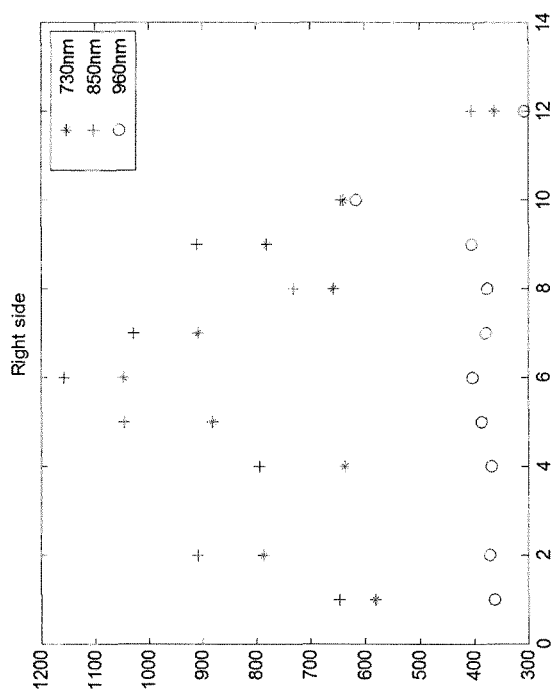
FIG. 26 is a chart representing edema monitoring device results for raw intensity measurements at 3 cm source detector separation on the right side of a human patient's brain.

Average of raw intensity measurements at 730, 850 and 960 nm wavelengths at 3 cm source detector separation on the right side of the head during 12 consecutive measurements collected every 6 hours from Patient 1 is shown in FIG. 26. For the same subject and conditions, the change in oxygenated ($HbO_2$) and deoxygenated hemoglobin (Hb) and water content extracted using MBLL is presented in FIG. 27. Here only the right side measurements are used because proper placement of the sensor on the left side was not possible. On the 3rd and 11th recordings, the recordings were either saturated or too noisy which may be because of a loss of coupling of the sensor with the skin.

Figure 27:
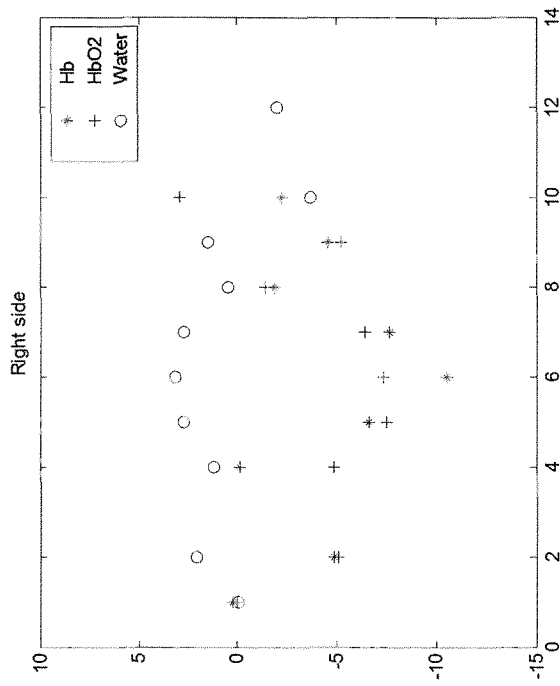
FIG. 27 is a chart representing edema monitoring device results for change in blood (Hb and $HbO_2$) and water contents of a human patient's brain.

From the patient log, it was found that around the time the first recordings was obtained, patient had facial edema, on the 2nd, 3rd and 4th recordings CSF drainage was performed, and on the 6th recording eye edema was observed. The patient had an overall GCS score of 3 during the corresponding 3 days of data collection. During this time ICP recordings got higher during the 6th and 7th recordings as compared to the previous recordings which lowered gradually until 12th recording. This change in intracranial pressure was also reflected in both the raw intensity measurements (FIG. 26) and also in blood and water level changes (FIG. 27).

Figure 29:
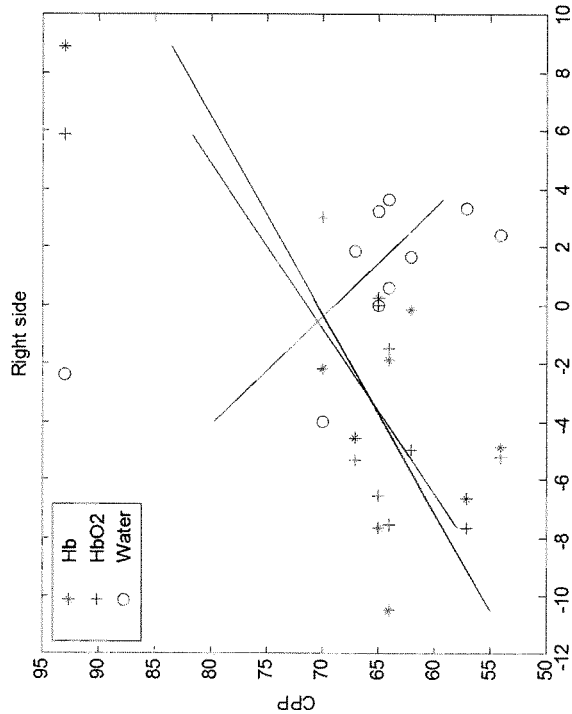
FIG. 29 is a chart representing edema device recordings vs CPP values.
Figure 28:
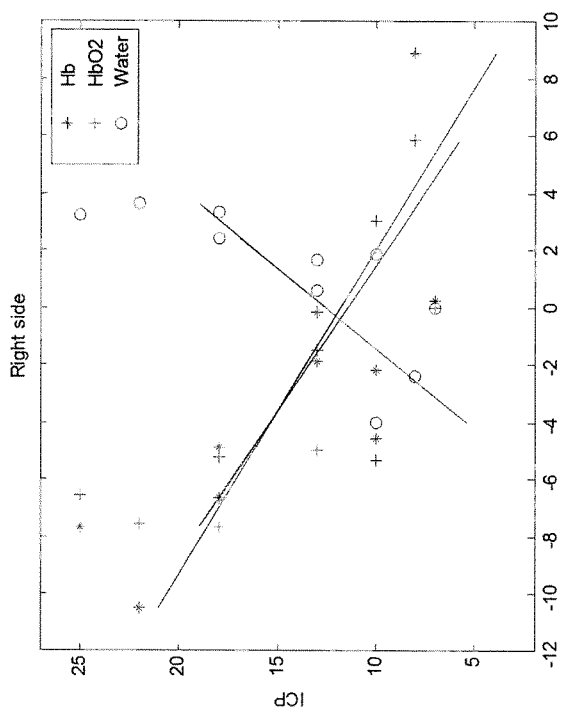
FIG. 28 is a chart representing edema device recordings vs ICP values.

Further analysis was performed separately on the correlations of ICP and cerebral perfusion pressure (CPP) with $HbO_2$, Hb and water content. The correlation results are summarized in Table 1. In FIGS. 28 and 29, edema device recordings vs ICP and CPP values for Patient 1 at different recording sessions are shown. High correlation values were observed between the edema monitoring device recordings and physiological parameters (ICP and CPP), especially for this patient where there was a lot of change observed in ICP (from 7 to 25) and CPP values. Since GCS scores remained unchanged during the course of the recordings, no further correlational analysis on GCS and edema device recordings was performed.

TABLE 1

Correlation coefficient (R) between ICP and CPP values and various edema monitoring measurements for Patient 1 (right side recording)

|  | $HbO_2$ | Hb | Water |
|---|---|---|---|
| ICP | R = −0.74 | R = −0.77 | R = 0.74 |
| CPP | R = 0.78 | R = 0.75 | R = −0.65 |

Patient 2: The second patient was a 65 year old white male who was in a motorcycle accident when driving without a helmet. The main injury site on this patient was on the right side of the brain where edema and hematoma were developed and removed through neurosurgery. The sensor was secured on the patient's forehead with adhesive tape and 20 minutes of data was collected every 6 hours within the 72 hour period after the start of the data collection protocol at 2 Hz from contralateral sides of the brain. Neurological and physiological measurements including GCS scores and ICP and CPP values were recorded at the same day and time points with the edema monitoring recordings.

Figure 31:
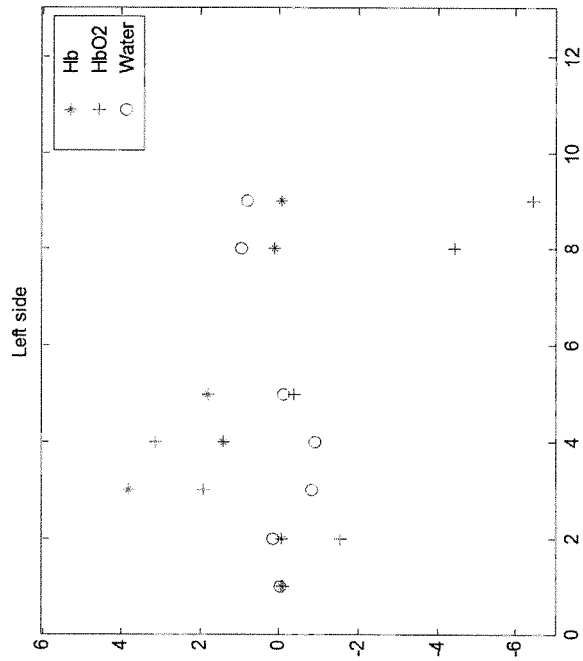
FIG. 31 is a chart representing edema monitoring device results for change in blood (Hb and $HbO_2$) and water contents of a human patient's brain.
Figure 30:
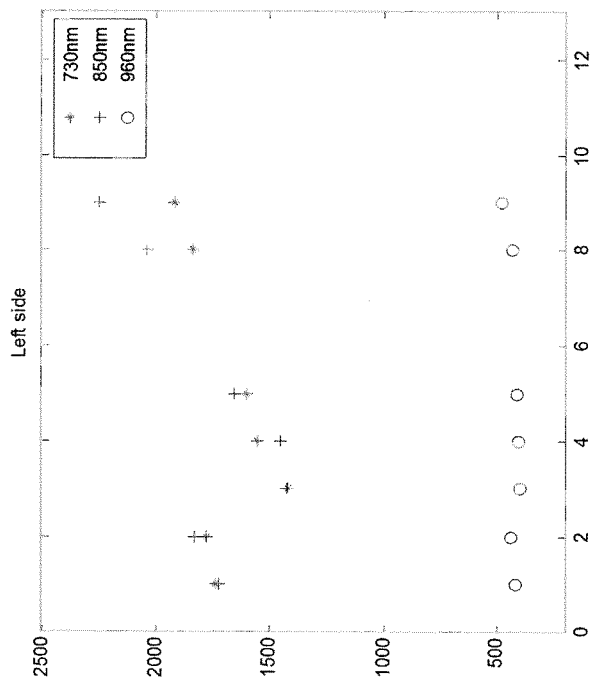
FIG. 30 is a chart representing edema monitoring device results for raw intensity measurements at 3 cm source detector separation on the right side of a patient's brain.

For this patient, injury was on the right side of the head. Moreover, there were bruises on the skin of the right forehead which caused the signal levels to be too low and not reliable on this side. The average of raw intensity measurements at 730, 850 and 960 nm wavelengths at 3 cm source detector separation on the left side of the head is shown in FIG. 30. The change in $HbO_2$, Hb and water content is shown in FIG. 31. Over the 12 recordings (every 6 hours within 3 days period), the noisy or saturated recordings or when the ICP bolt is taken out (after 9th recording) are not shown in FIGS. 30 and 31. The GCS scores for this patient during the recording period was 10, patient was opening his eyes time to time, moving his arms and legs, but not following commands most of the time. After the 9th recording, the patient's condition was mostly stabilized and the ICP bolt was taken out. During the whole recording period the ICP values were mostly very low.

Figure 33:
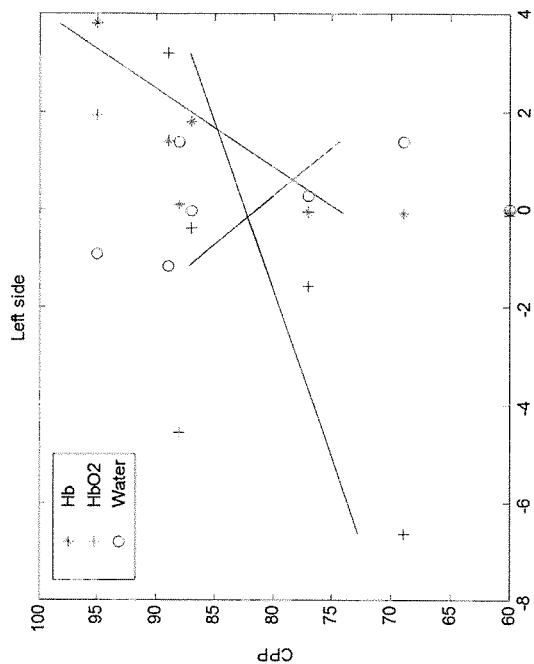
FIG. 33 is a chart representing edema device recordings vs CPP values.
Figure 32:
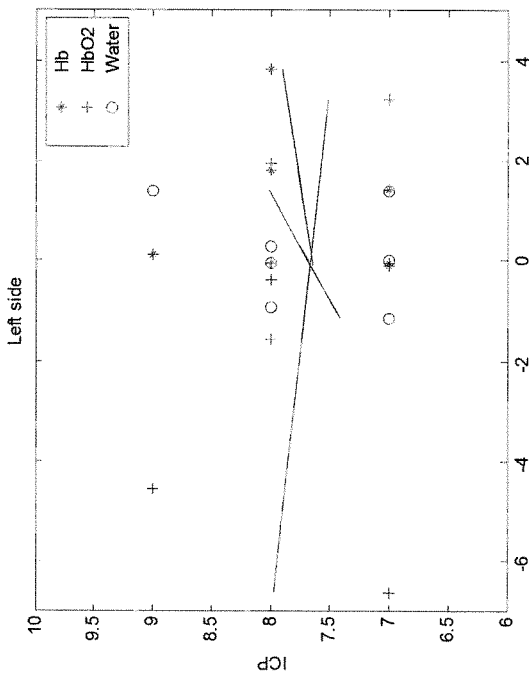
FIG. 32 is a chart representing edema device recordings vs ICP values.

A correlational analysis between ICP and CPP values with $HbO_2$, Hb and water content as measured by the edema monitoring device was performed and is summarized in Table 2. In FIGS. 32 and 33, edema device recordings in terms of $HbO_2$, Hb and water content vs ICP and CPP values at different recording sessions are shown. Since the patient was mostly stabilized during the whole recording session, there was not much change in the ICP values (mainly around 7-9) and some change was observed in CPP, therefore correlation with edema monitoring device recordings was found to be moderate with CPP values.

TABLE 2

Correlation coefficient (R) between ICP and CPP values and various edema monitoring measurements for Patient 2 (left side recording)

|  | HbO2 | Hb | Water |
|---|---|---|---|
| ICP | R = −0.21 | R = 0.12 | R = 0.31 |
| CPP | R = 0.40 | R = 0.73 | R = −0.40 |

Example 3

Animal (Piglet) Testing

For purposes of further testing the NIR based brain monitoring system having three wavelength light sources and signal processing algorithms, the development of cerebral edema following hypoxia was monitored and an assessment of cerebral autoregulation in a piglet study was performed.

Edema Monitoring: After obtaining relevant IACUC approval, newborn piglets were exposed to hypoxia (HI) [$FiO_2$ 0.07 for 1 hr and hypotension (40% decrease in systolic BP)], then returned to $FiO_2$ 0.21 to restore $O_2$ and BP for 4 hrs (HI-4Hr; n=2). Anesthesia was induced with 4% Isoflurane and maintained with 79% nitrous oxide, fentanyl analgesia and vecuronium paralysis. Normoxic piglets (Nx-4Hr; n=2) were ventilated with $FiO_2$ 0.21. One of the NIR based split sensors was placed on the piglet head (the other one is placed on the back of the piglet), and recordings were made at 3 different wavelengths (730 m 850 and 940 nm) to couple changes in light attenuation to changes in deoxyHb, oxyHb and water, respectively. The height of the cerebrospinal fluid column was recorded at the end of the recording, with values ≥11 cm $H_2O$ representing an elevated ICP based on reported human infant data. Cerebral water content (ml water/gram tissue) was determined as wet-dry weights/wet weight of samples of the cerebral cortex measured before and after incubation for 72 hrs at 90° C. Results are expressed as M±SEM.

Figure 34:
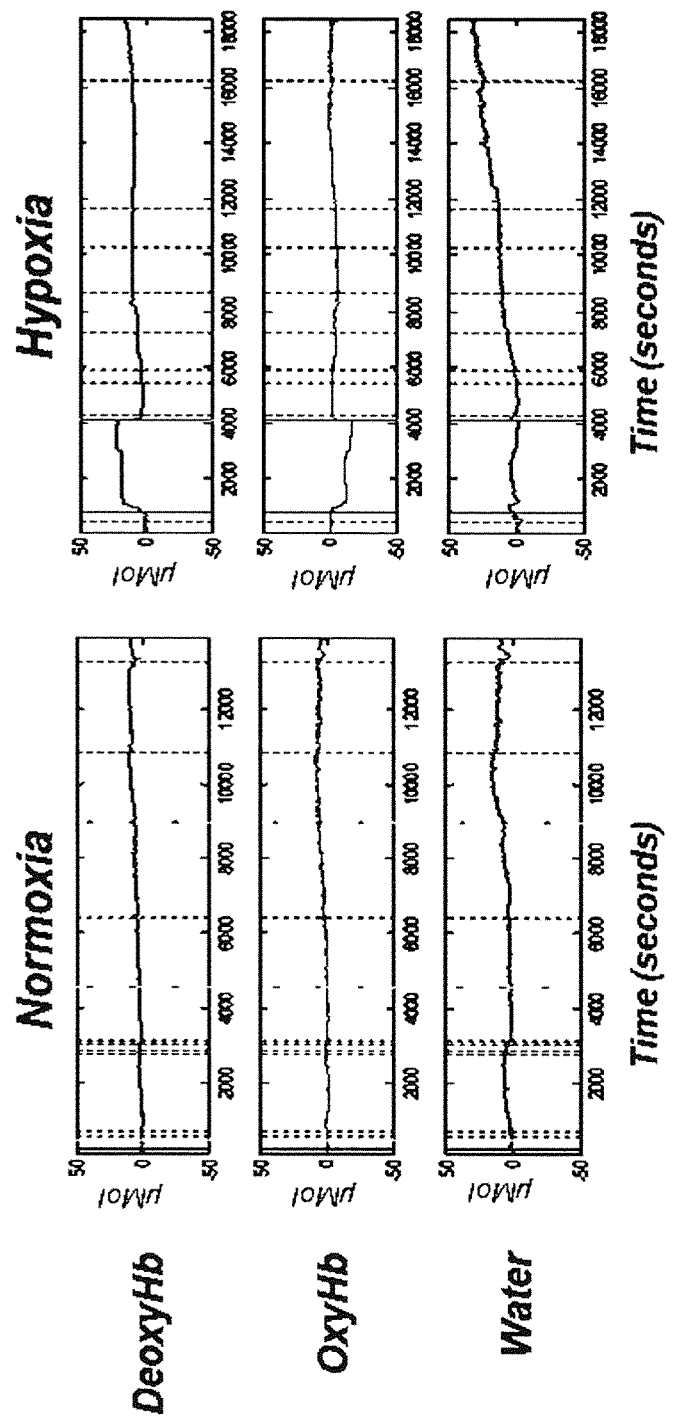
FIG. 34 is charts representing overall recordings for Nx and HI piglets.
Figure 35:
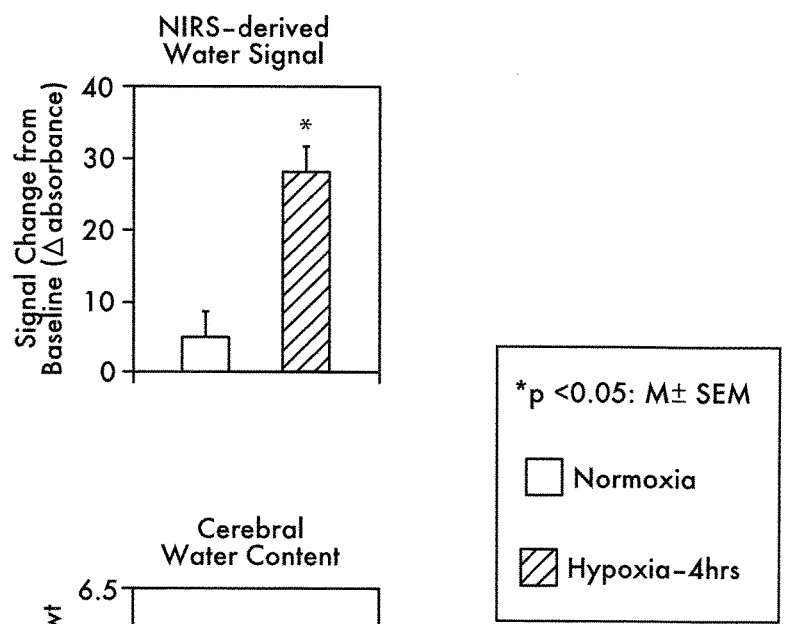
FIG. 35 is a graph showing average NIRS water signal for Nx and HI piglets.
Figure 36:
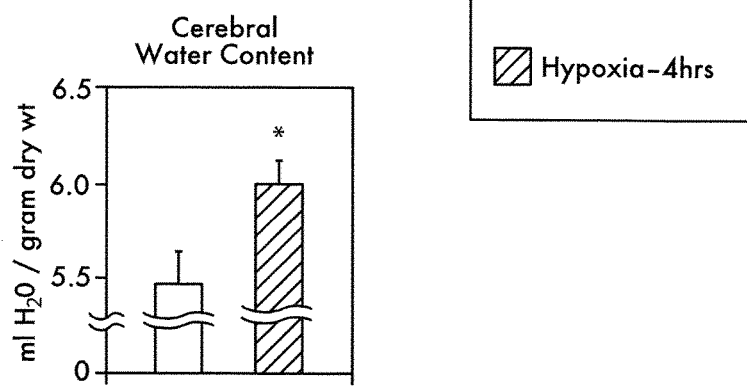
FIG. 36 is a graph showing ICP for Nx and HI piglets.
Figure 37:
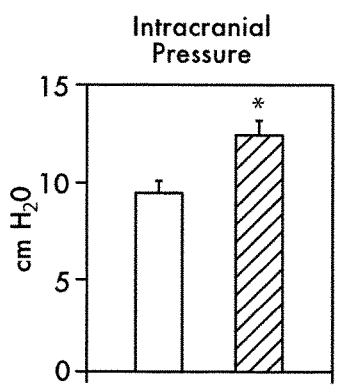
FIG. 37 is a graph showing wet/dry ratio measurements for Nx and HI piglets.

FIG. 34 shows a representative tracing obtained from one HI and one Nx piglet. DeoxyHb signal increased and oxyHb signals decreased predictably with the onset of and during hypoxia, and returned to baseline after reoxygenation. Arterial blood gas values during the period confirmed hypoxemic $PaO_2$ values. Water signal increased progressively from baseline following the hypoxia-ischemia period, indicating cerebral edema. NIRS-derived cerebral water signal (units) was 25.88±3.77 in HI-4Hr (n=6) and 5.42±4.48 in Nx-4HR (n=5) piglets. Overall, all HI piglets and none of the Nx piglets had elevated ICP at 4 hours post HI (12.7±1.86 vs 9.5±1.0 cm $H_2O$). Cerebral water content (ml water/gram tissue) was 5.83±0.11 in HI and 5.45±0.29 in Nx-4Hr piglets. The data shows that the increase in NIRS-derived cerebral water signal correlated well with increases in both cerebral water content and intracranial pressure (see FIGS. 35, 36 and 37).

Significant correlations between NIRS-derived cerebral water signal and the ICP measurements ($R=0.75$, $p<0.05$) and the cerebral water content ($R=0.74$, $p<0.01$) were also found as shown in FIG. 41. These results suggested that NIRS-derived water signal values can reflect the change in the amount of cerebral water content and the increased ICP related with it.

Figure 38:
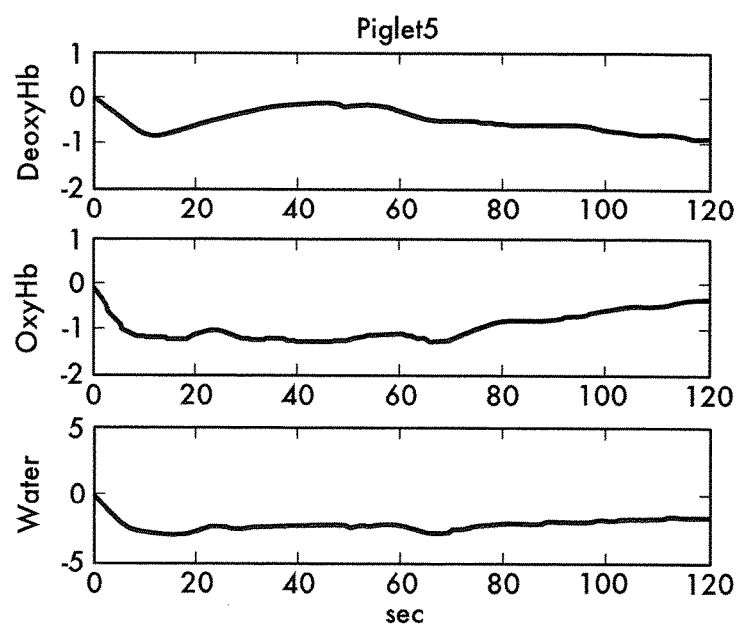
FIG. 38 is a chart representing averaged 2 minute signal epochs following drug injection for Hypoxic piglet.
Figure 39:
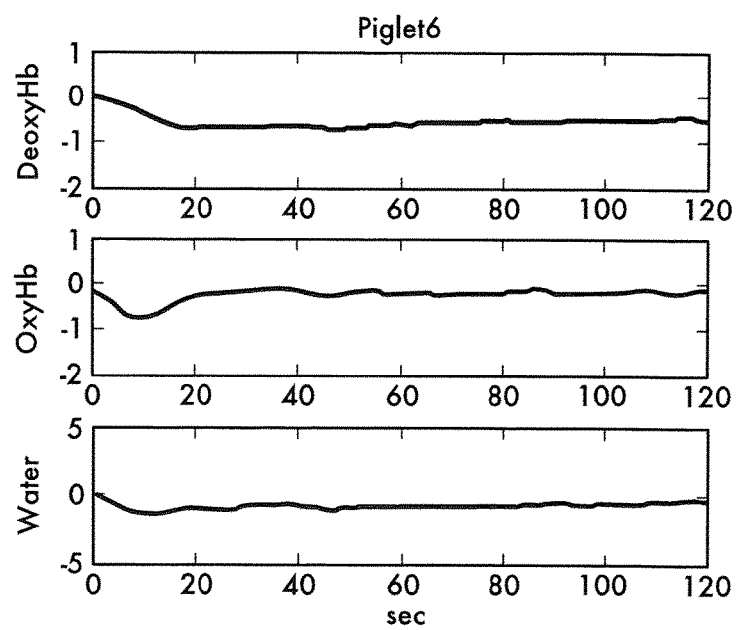
FIG. 39 is a chart representing averaged 2 minute signal epochs following drug injection for Normoxic piglet.

Cerebral Autoregulation Assessment: In the experiment explained above during the length of the recording at certain time intervals, a combination of anesthetic agents and saline was injected intravenously. Following the injection of the medication combination, a certain type of signal change (a gamma type signal reduction in values) in all the NIRS recordings (Hb, $HbO_2$ and water content) is observed for a period of ~2 min. As an example, averaged signal epochs for a Hypoxic and a Noimoxic piglet are shown in FIGS. 38 and 39.

It was expected that more reduction in the signal following drug injection will be observed in hypoxic piglets as compared to the normoxia cases due to the change in the cerebral autoregulation of piglets that are exposed to hypoxia. For purposes of testing this hypothesis, 2 minute data epochs were extracted directly after each medication and saline injection on the recordings obtained from the head. Each epoch is baseline corrected using 1 second of data prior to injection (mean of the pre-injection is subtracted from the epoch). For the comparison of the dip in Nx and HI cases, the minimum value within the first 1 minute of the epoch for each chromophore, Hb, $HbO_2$ and water was extracted.

Figure 40:
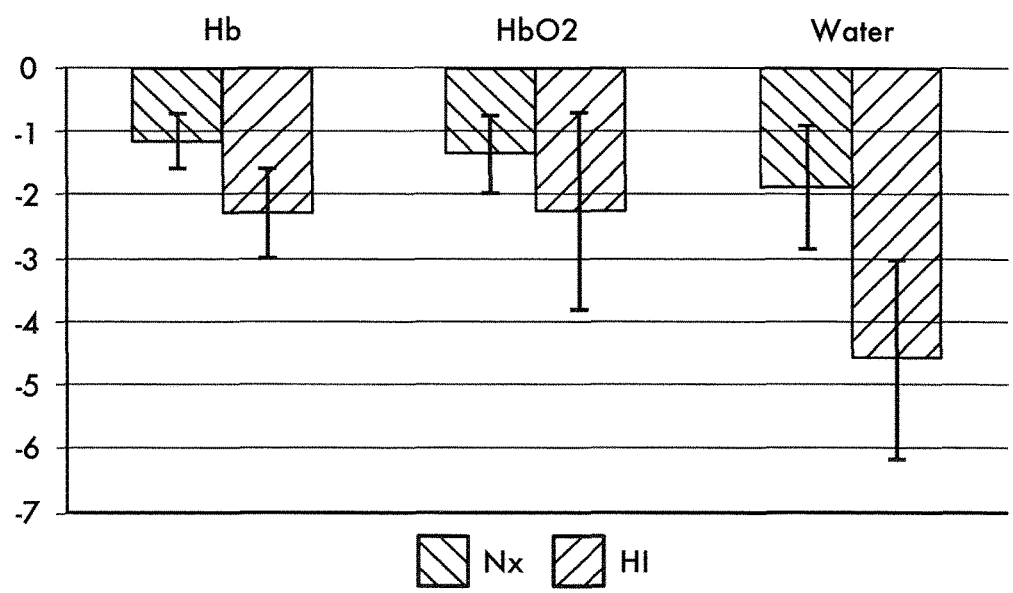
FIG. 40 is a graph showing averaged minimum dip values in Hb, HbO2 and water signal epochs following drug injection for Hypoxic and Normoxic piglets.
Figure 42:
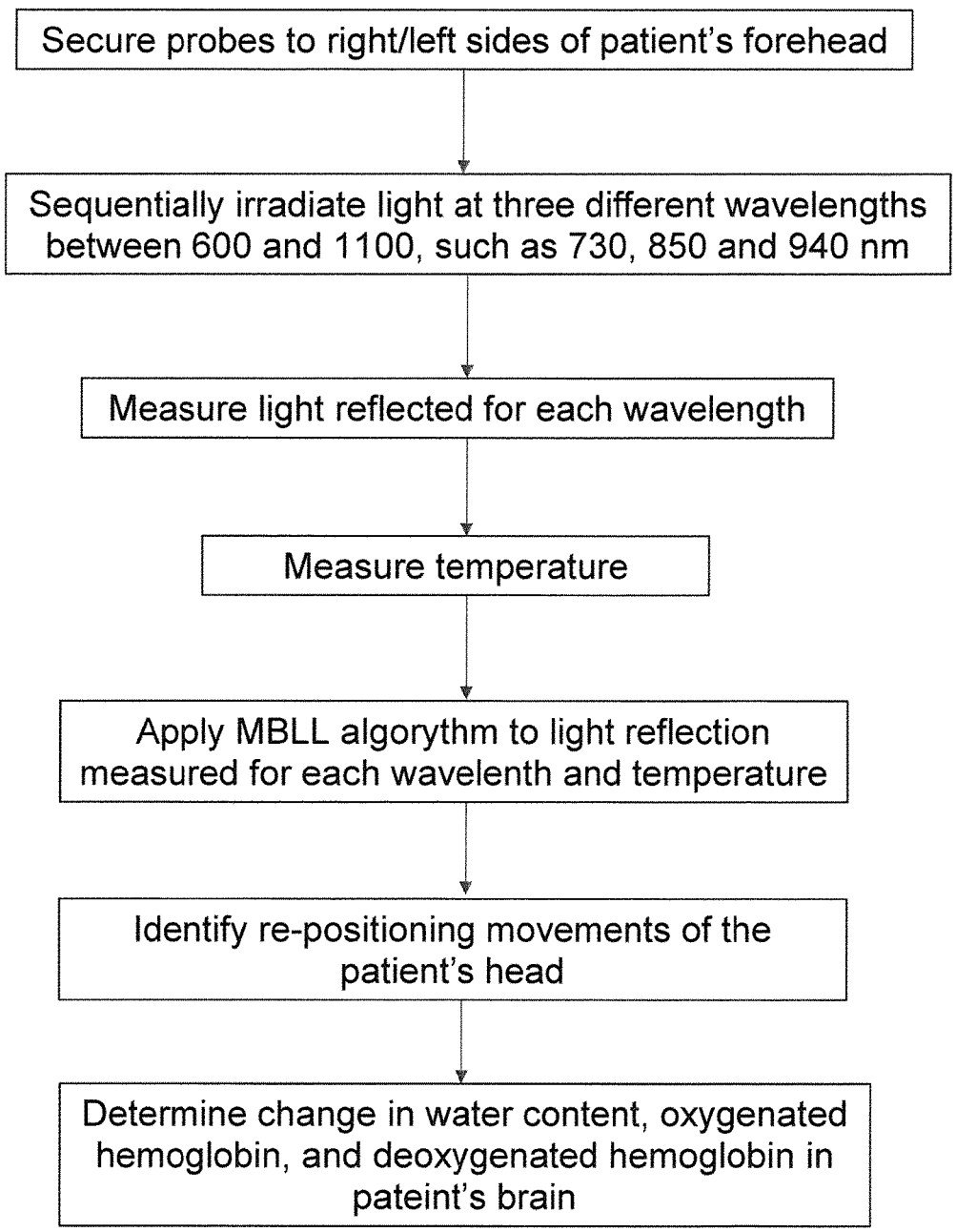
FIG. 42 is a flow chart showing a process for quantitatively monitoring and evaluating changes in water and hemoglobin contents in a patient's brain.

The minimum dip values in Nx and HI piglets for all the chromophores are summarized in Table 3. As hypothesized, the HI piglets resulted in more reduction in all of the chromophores (Hb, $HbO_2$ and water where water provided the most prominent change) following saline and drug injection as compared to Nx piglets due to differences in cerebral autoregulation following a hypoxic event (FIG. 40). These results suggest that the proposed NIR based brain monitoring device with its capabilities in monitoring of Hb, $HbO_2$ and water content changes can be used in the assessment of cerebral autoregulation. This capability provides clinicians with very important information on the existence/absence of a prior hypoxic event. By injecting saline and medication to the patient which is already a common procedure in clinically ill infants, clinicians can monitor changes in the signals as measured by the proposed device for a short period of time (~2 min) and decide if a hypoxic event has happened before or not, or when did it happen or they can also monitor treatment outcomes not only for reduction or edema development, but also, in returning back to normal cerebral autoregulation levels.

TABLE 3

Averaged minimum values in Hb, HbO2 and water after medication injection for Nx and HI piglets

|    | Hb | HbO2 | Water |
|----|-----|------|-------|
| Nx | −1.15 ± 0.41 | −1.35 ± 0.60 | −1.92 ± 0.98 |
| HI | −2.28 ± 0.71 | −2.28 ± 1.56 | −4.63 ± 1.58 |

Early detection and rapid treatment of brain edema is critical to prevent development of severe brain injury. The embodiments disclosed above provide a non-invasive testing device for use by clinicians to detect and monitor the progress of brain edema. In addition, embodiments disclosed above provide information on cerebral autoregulation that can guide certain therapies in case of a prior hypoxic event. The hand-held non-invasive device for the monitoring of brain edema and cerebral autoregulation according to embodiments disclosed herein significantly enhance and aid current clinical practices/treatments by: i) providing accurate and immediate clinical decision support as allowing to triage patients with edema; ii) allowing frequent monitoring of the progress of brain edema and a reduction of unnecessary invasive surgeries; and iii) measuring cerebral autoregulation to provide information on the existence of prior hypoxic event to guide in therapeutic interventions.

Accordingly, embodiments of the NIR based brain monitoring device disclosed herein use three light sources at 730 nm, 850 nm and 940 nm (or 960 nm) wavelengths to monitor changes in Hb, $HbO_2$ and water content in the brain and includes a thermistor to monitor temperature changes. The device utilizes additional signal analysis components to adjust parameters (molar extinction coefficients and DPF values) in the MBLL algorithm for changes related to wavelength, source-detector separation, temperature and oxygen saturation and also for head movement or laying position related artifacts. Methods are provided for the detection and monitoring of cerebral edema and for the assessment of cerebral autoregulation.

While the principles of the invention have been described above in connection with specific devices, systems, and/or methods, it is to be clearly understood that this description is made only by way of example and not as limitation. One of ordinary skill in the art will appreciate that various modifications and changes can be made without departing from the scope of the claims below. Accordingly, the specification and figures are to be regarded in an illustrative rather than a restrictive sense, and all such modifications are intended to be included within the scope of the present invention.

What is claimed is:

1. A portable, point-of-care, near-infrared-based imaging device for quantitatively monitoring and evaluating changes in water and hemoglobin content in a patient's brain, comprising:
   a pair of separate and identical probes, one of said probes being adapted for non-invasive placement against a left side of a forehead of a patient and the other one of said probes being adapted for separate non-invasive placement against a right side of the forehead of the patient, each of said probes having a light emitting diode (LED) light source mounted thereon for separately and sequentially irradiating light at three different pre-determined wavelengths between 600 and 1100 nm, each of said probes having a pair of photo detectors mounted thereon at different predetermined distances from said light source for measuring an amount of light reflected during irradiation of light at each wavelength, and each of said probes having a temperature sensor mounted thereon; and
   at least one electronic processing unit for receiving measurements from said probes of light reflected for each of the wavelengths and temperature and for using the measurements to determine a change in water content, a change in oxygenated hemoglobin, and a change of deoxygenated hemoglobin separately for each of the right and left hemispheres of the patient's brain;
   wherein each of said probes includes a flexible circuit board able to flex to match a contour of a patient's forehead, a cushioning material covering the flexible circuit board, and an adhesive for securing the probe in a non-invasive manner on the patient's forehead;
   wherein the three different predetermined wavelengths include a wavelength of 730 nm for use in determining changes in deoxygenated hemoglobin content, a wavelength of 850 nm for use in determining changes in oxygenated hemoglobin content, and a wavelength of 940 or 960 nm for use in determining changes in water content;
   wherein said at least one electronic processing unit is configured to control operation of the light sources such that light is emitted at only one wavelength at a time and such that light is emitted at each of the three wavelenghts in a sequential manner;
   wherein said at least one electronic processing unit is configured to apply a modified Beer-Lambert law (MBLL) algorithm to determine relative changes in water, deoxygenated hemoglobin, and oxygenated hemoglobin over time based on changes of optical density detected for each of the three wavelengths;
   wherein information of temperature, wavelength of light, light source to photo detector spacing, left and right hemisphere measurements and oxygen saturation is utilized by said algorithm to adjust the determination of relative changes in water, deoxygenated hemoglobin, and oxygenated hemoglobin; and
   wherein said at least one electronic processing unit is configured to automatically identify re-positioning movements of the patient's head based on changes in water content, changes in oxygenated hemoglobin content, and changes in deoxygenated hemoglobin content that exceed a pre-determined threshold within a pre-determined amount of time.

2. A method of quantitatively monitoring and evaluating changes in water and hemoglobin contents in a patient's brain, comprising the steps of:
   using the portable, point-of-care, near-infrared-based imaging device according to claim 1 by securing a first probe of the device in a non-invasive manner on a left forehead of a patient and separately securing a second probe of the device on a right forehead of the patient;
   electronically controlling at least one light source mounted on each one of the probes to separately and sequentially irradiate light at three different pre-determined wavelengths between 600 and 1100 nm;
   electronically controlling at least one photo detector mounted on each one of the probes at a predetermined distance from said at least one light source to measure an amount of light reflected detected by the at least one photo detector for each wavelength;
   measuring temperature with a temperature sensor mounted on each one of the probes;
   applying an algorithm with at least one electronic processing unit in communication with the probes to measurements of light reflection for each of the wavelengths and temperature; and
   determining and displaying on a display a change in water content, a change in oxygenated hemoglobin, and a change of deoxygenated hemoglobin separately for each of the right and left hemispheres of the patient's brain;
   wherein the three different predetermined wavelengths include a wavelength of 730 nm for use in determining changes in deoxygenated hemoglobin content, a wavelength of 850 nm for use in determining changes in oxygenated hemoglobin content, and a wavelength of 940 nm for use in determining changes in water content;
   wherein said step of controlling the at least one light source includes causing the at least one light source to sequentially emit light only at a wavelength of 730 nm for a pre-determined period of time, to emit light only at a wavelength of 850 nm for a pre-determined period of time, and to emit light only at a wavelength of 940 nm for a pre-determined period of time followed by a period of no light emission before repeating the sequence;
   wherein said algorithm applying step includes application of a modified Beer-Lambert law (MBLL) algorithm to determine relative changes in water, deoxygenated hemoglobin, and oxygenated hemoglobin over time based on changes of optical density detected for each of the three wavelengths, said algorithm applying step including the use of information of temperature, wavelength of light, light source to photo detector spacing, left and right hemisphere measurements, and oxygen saturation to adjust the determination of relative changes in water, deoxygenated hemoglobin, and oxygenated hemoglobin; and wherein said algorithm applying step includes automatically identifying re-positioning movements of the patient's head based on changes in water content, changes in oxygenated hemoglobin content, and changes in deoxygenated hemoglobin content that exceed a pre-determined threshold within a pre-determined amount of time.

\* \* \* \* \*